(12) United States Patent
Hoff

(10) Patent No.: US 11,820,719 B2
(45) Date of Patent: Nov. 21, 2023

(54) SYSTEM FOR TREATING BIOMASS WITH A GAS

(71) Applicant: Advanced Substrate Technologies A/S, Randers SØ (DK)

(72) Inventor: Svend Hoff, Odder (DK)

(73) Assignee: Advanced Substrate Technologies A/S, Randers SO (DK)

( * ) Notice: Subject to any disclaimer, the term of this patent is extended or adjusted under 35 U.S.C. 154(b) by 829 days.

(21) Appl. No.: 16/483,255

(22) PCT Filed: Feb. 2, 2018

(86) PCT No.: PCT/EP2018/052603
§ 371 (c)(1),
(2) Date: Aug. 2, 2019

(87) PCT Pub. No.: WO2018/141888
PCT Pub. Date: Aug. 9, 2018

(65) Prior Publication Data
US 2020/0010379 A1 Jan. 9, 2020

(30) Foreign Application Priority Data
Feb. 3, 2017 (EP) ..................................... 17154555

(51) Int. Cl.
*C12M 3/00* (2006.01)
*C05F 3/00* (2006.01)
(Continued)

(52) U.S. Cl.
CPC ................. *C05F 17/60* (2020.01); *C05F 3/06* (2013.01); *C05F 5/002* (2013.01); *C05F 17/95* (2020.01);
(Continued)

(58) Field of Classification Search
CPC ........... C05F 3/06; C05F 5/002; C12M 47/06; C12M 41/40; C12M 33/16
See application file for complete search history.

(56) References Cited

U.S. PATENT DOCUMENTS

| 8,252,072 B2 * | 8/2012 | Dogru | ........................ C10J 3/30 48/77 |
| 2004/0120867 A1 * | 6/2004 | Dahms | ....................... C05B 7/00 422/184.1 |

(Continued)

FOREIGN PATENT DOCUMENTS

| DE | 202014000237 U1 | 2/2014 |
| WO | 02015945 A1 | 2/2002 |

(Continued)

Primary Examiner — Nathan A Bowers
(74) Attorney, Agent, or Firm — DINSMORE & SHOHL LLP

(57) ABSTRACT

A system and a method for treating biomass with a gas includes at least one conduit having at least one biomass inlet and at least one biomass outlet, at least one gas inlet and at least one gas outlet. The system further includes a transport unit configured to move the biomass through the conduit from the at least one biomass inlet to the at least one biomass outlet thereby defining a biomass transport direction. The system is configured such that gas flowing from the at least one gas inlet to the at least one gas outlet crosses the biomass transport direction.

17 Claims, 14 Drawing Sheets

(51) Int. Cl.
*C05F 17/60* (2020.01)
*C05F 17/95* (2020.01)
*C05F 3/06* (2006.01)
*C05F 5/00* (2006.01)
*C12M 1/26* (2006.01)
*C12M 1/34* (2006.01)
*C12M 1/00* (2006.01)
*C12M 1/04* (2006.01)

(52) U.S. Cl.
CPC ............ *C12M 1/04* (2013.01); *C12M 33/16* (2013.01); *C12M 41/12* (2013.01); *C12M 41/26* (2013.01); *C12M 41/34* (2013.01); *C12M 41/40* (2013.01); *C12M 45/06* (2013.01); *C12M 47/06* (2013.01)

(56) References Cited

U.S. PATENT DOCUMENTS

2009/0221814 A1* 9/2009 Pschorn .................... D21C 3/22
                                                          422/600
2011/0278150 A1* 11/2011 Mulqueen ............... C10B 57/02
                                                          202/99

FOREIGN PATENT DOCUMENTS

| WO | 2009045653 | A2 | 4/2009 |
| WO | 2009108773 | A2 | 9/2009 |
| WO | 2014047097 | A1 | 3/2014 |
| WO | 2014124401 | A1 | 8/2014 |
| WO | 2016004482 | A1 | 1/2016 |
| WO | 2016094594 | A1 | 6/2016 |
| WO | 2016116113 | A1 | 7/2016 |

* cited by examiner

SYSTEM FOR TREATING BIOMASS WITH A GAS

CROSS-REFERENCE TO RELATED APPLICATIONS

This application is the U.S. national stage of PCT/EP2018/052603 filed Feb. 2, 2018, which claims priority of European Patent Application 17154555.1 filed Feb. 3, 2017 each of which is hereby incorporated by reference in its entirety.

FIELD OF THE INVENTION

The present invention relates to a system for treating biomass with a gas, such as a steam comprising nitrogen, a method for treating biomass with steam comprising nitrogen, a method for treating biomass with air, and the use of the system as a drying unit and/or a biofilter.

BACKGROUND OF THE INVENTION

Biomass may play a key role when replacing fossil energy sources with renewable energy sources. Firstly, biomass may be converted into liquid fuels and biogas that are direct substitutes of the fossil based fuels. Secondly, biomass may be converted into products that can be used as fertilizers or growing medium, such as substrates for mushrooms.

The process of converting biomass to fuels or other products will depend on the type of biomass. Biomass based on plant matter, such as trees and agricultural crops as straw, are also referred to as lignocellulosic biomass. Lignocellulosic biomass comprises lignocellulose, within which fermentable sugars are bonded to lignin. The lignin forms the structural backbone of a plant, whereas the sugars are the energy source of the biomass which may be fermented to fuels or fuel precursors such as ethanol. However, to access the fermentable sugars from a plant, the bond to lignin must be broken.

A key step in the conversion of lignocellulosic biomass is therefore to extract lignin from the biomass. This is conventionally done by treating the biomass with a gaseous or aqueous ammonia solution. Ammonia causes lignin to dissolve, whereas the cellulose is retained in the solid phase, and the solubilised lignin is then removed from the system such that is does not recondense onto the biomass. This step is also referred to as ammonia pretreatment.

The efficiency of an ammonia pretreatment is reflected in the degree of lignin removed as well as the retention time of the treatment. The efficiency will depend on the operational conditions, such as temperature and pressure, as well as the ammonia concentration, the contact time, and the degree of contact surface area between ammonia and the biomass.

WO1609494 [1] describes a system for pretreatment of biomass, where the biomass is extruded through a reaction chamber, while being exposed to chemicals, elevated temperature and pressure. The biomass feedstock may be hydrated and non-compacted. The method results in a rapid retention time of about 20 seconds.

WO 2016/116113 [2] describes a system for pretreatment of biomass, where steam comprising nitrogen is sucked through the biomass, which may be cutted straw or biomass pretreated in other ways. The steam comprising nitrogen is effectively ammonia at the operational conditions of 60-95° C. and pH 7-9 or 7-10. To improve the efficiency of the system, the steam comprising nitrogen may be derived from a dryer, where the dryer is the unit where the raw biomass is dried before the nitrogen treatment. The retention time of the nitrogen treatment is between 20 minutes to 12 hours.

Despite the advances within pretreatment of biomass, there is a need for more efficient biomass pretreatment. Furthermore, ammonia is a potential hazardous chemical, and there is a need for pretreatment methods, where the environmental emission from the process may be controlled, and the work safety improved by reducing the risk of human exposure.

SUMMARY OF THE INVENTION

The present disclosure provides a system for treating biomass, where a surprisingly high efficiency of the treatment is obtained by improving the contact surface area between the biomass and treatment gas. The improved contact surface area results in a more time- and cost-efficient treatment, and further facilitates that larger quantities of biomass may be efficiently treated. The system and method is therefore especially suitable for large-scale and industrial scale treatment of biomass.

A first aspect of the disclosure relates to a system 1, said system comprising:
  at least one conduit 2 comprising:
    at least one biomass inlet 3 and at least one biomass outlet 4,
    at least one gas inlet 5 and at least one gas outlet 6, and
  a transport unit 7,8 configured to move the biomass through the conduit(s) from the at least one biomass inlet 3 to the at least one biomass outlet 4 thereby defining a biomass transport direction,
  wherein the system is configured such that gas flowing from the at least one gas inlet 5 to the at least one gas outlet 6 crosses the biomass transport direction.

In a preferred embodiment of the first aspect, the gas is steam. In another preferred embodiment of the first aspect, the gas is air. In another preferred embodiment of the first aspect, the gas is an exhaust gas.

Thus, a preferred aspect of the disclosure relates to a system 1, said system comprising:
  at least one conduit 2 comprising:
    at least one biomass inlet 3 and at least one biomass outlet 4,
    at least one steam inlet 5 and at least one steam outlet 6, and
  a transport unit 7,8 configured to move the biomass through the conduit(s) from the at least one biomass inlet 3 to the at least one biomass outlet 4 thereby defining a biomass transport direction,
  wherein the system is configured such that steam flowing from the at least one steam inlet 5 to the at least one steam outlet 6 crosses the biomass transport direction.

A second aspect of the disclosure relates to a method for treating biomass with steam comprising nitrogen, said method comprising the steps of:
  a) providing biomass 3,
  b) providing at least one conduit 2 comprising a flow of steam comprising nitrogen,
  c) introducing the biomass into a first end 3 of the at least one conduit 2,
  d) transporting the biomass along the conduit by transport means,
  e) removing the biomass from a second end 4 of the conduit 2,
  whereby the biomass is treated with a steam comprising nitrogen.

A third aspect of the disclosure relates to a method for treating biomass with air, said method comprising the steps of:
a) providing biomass,
b) providing at least one conduit 2 comprising a flow of air,
c) introducing the biomass into a first end 3 of the at least one conduit,
d) transporting the biomass along the conduit by transport means 7,8,
e) removing the biomass from a second end 4 of the conduit,
whereby the biomass is treated with air.

A fourth aspect of the disclosure relates to the use of the system according to the third aspect as a drying unit and/or a biofilter.

BRIEF DESCRIPTION OF THE DRAWINGS

The invention will in the following be described in greater detail with reference to the accompanying drawings.

DETAILED DESCRIPTION OF THE INVENTION

Ammonia pretreatment is an essential step in converting raw lignocellulosic biomass into applicable products such as biofuels, fertilisers, and substrates for agricultural purposes. By the term "ammonia pretreatment" is meant a process, where lignin is extracted from a biomass using a liquid or gas effectively comprising ammonia. Steam comprising nitrogen (N) will effectively comprise ammonia. Thus, treating a biomass with a steam comprising nitrogen is an example of ammonia pretreatment. Ammonia pretreatment may also be referred to as "ammonia N treatment" or "N-steam treatment".

By ammonia treatment of straw it is possible to increase the content of raw protein from 3.3% to 8% in wheat straw, from 4% to 6.9% in barley straw, and increase the digestible energy content from 7.5 to 9.5 MJ/kg of dry matter.

Figure 1:
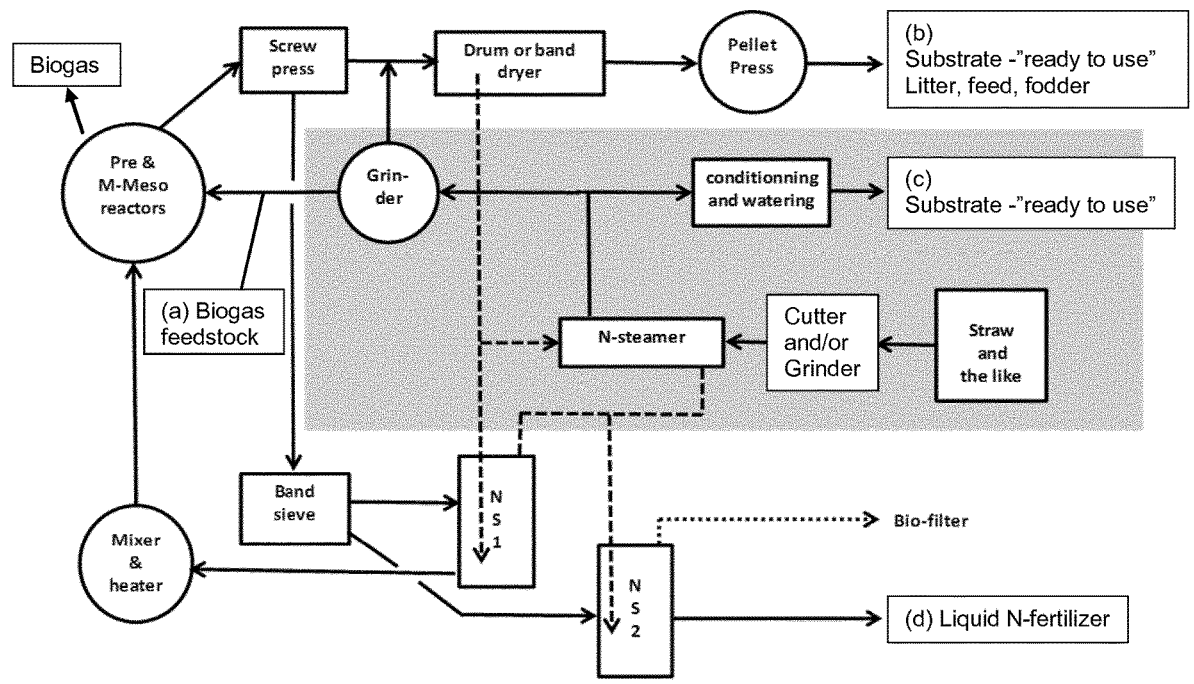
FIG. 1 shows an example of biomass conversion system comprising a N-steamer, where biomass such as straw, is converted into products with increased value, e.g. increased protein content, and used for (a) biogas feedstock, (b-c) agricultural substrates, litter, feed/fodder, and (d) fertilizer.

FIG. 1 shows an example of a system, where biomass such as straw, may be converted into products, such as fibers, with increased value, e.g. increased protein content, and used for agricultural substrates, fertilizer, feed/fodder, and biofuel precursor. The feedstock in FIG. 1 may be any biomass rich in carbon, including complex waste such as complex agricultural waste, e.g. category II waste including crop residues, straw, grass and the like.

The treatment steps of the system in FIG. 1 is illustrated by arrows, where broken lines represent gases (flow and utilization of e.g. N-steam), and solid lines represent solid materials (flow and utilization of e.g. straw). The feedstock biomass is first cut and/or grinded to a desired length and/or size, indicated to take place in the "cutter" or "cutter and/or grinder" shown in FIG. 1. Subsequently, the biomass is exposed to the ammonia pretreatment indicated to take place in the "N-steamer" shown in FIG. 1.

By the term "N-steamer" is meant the system, or apparatus, configured for treating the biomass with steam comprising nitrogen. However, without further modifications of the system, the system may be applied to treat the biomass with any other gas, i.e. the gas inlet and gas outlet may be applicable for steam as well as any other gas, such as air or a waste gas or exhaust gas from another unit. Thus, the term "N-steamer" as used herein, may be used interchangeably with the term "gas steamer".

From the N-steamer, the treated solid material with increased value can be diverted to one or more of:
a) a grinder and subsequently a biogas reactor (indicated as "Pre & M-Meso reactors" in FIG. 1), where the biogas feedstock is converted to biogas,
b) a grinder and/or dryer and subsequently a pellet press to produce pellets for substrate or litter (indicated as "ready to use" substrate and litter in FIG. 1), and/or
c) a conditioning and/or watering device to produce substrates directly utilisable as e.g. mushroom growth substrate (indicated as "ready to use" substrate in FIG. 1).

If the feedstock biomass has already been grinded in the step before the N-steamer, a further grinding step may not be necessary. For example, as indicated in the process (b) above, the solid material from the N-steamer may be diverted directly to a dryer without be subjected to a further grinding step.

By the term "ready to use" is meant a substrate or material form that can be stored until time of use. For example a mushroom substrate that is ready to use will be readily applicable for use by just adding water and mycelium. The substrates obtained as shown in FIG. 1 will contain nutrients, i.e. protein, C, N, P, K and more from the original biomass. The substrates, or biomass fibers, may further be processing into an advantageous form, e.g. by conditioning and watering or pellet pressing whereby the form is configured to be porous such that the material can absorb and retain water easily and fast, and further be porous for percolation and evaporation such that creation of anaerobic zones are avoided.

The produced pellets may also be used as litter pellets for horses, poultry or cattle. The pellets may also be produced from partly degasified biomass, i.e. the dried fiber solids of the biomass that has been through the Pre & M-Meso reactors, as indicated by the solid arrows in FIG. 1. Optionally, the partly degasified biomass from the reactor are transferred or moved from the reactor to the dryer and subsequently to the pellet press, using a "screw press" as indicated in FIG. 1.

From the N-steamer, the used steam may be further stripped of nitrogen, and the recovered nitrogen may be converted to liquid nitrogen fertilizer. Thus, a fertilizer comprising nitrogen (indicated as (d) in FIG. 1) may be an additional product of the method shown in FIG. 1.

The process of removing volatile nitrogen containing compounds, typically by evaporation, is referred to as "N-stripping", and the process is indicated to take place in the units "NS1" and "NS2" in FIG. 1. One or more stripping units configured for different operational conditions may be applied. Thus, in FIG. 1 the N-steam is diverted to NS1 for stripping and sanitation (to reduce the N-load on the system), and/or NS2 if the N-steam is no longer very warm.

The stripped gaseous nitrogen is subsequently absorbed in absorbers in NS2 and fixed in a liquid NS-fertilizer by e.g. adding $H_2SO_4$.

The water part from the absorbers that is not fixed in the NS-fertilizer may be collected, and used in the reactors for producing biogas feedstock. The water part will comprise some nitrogen, and the N-water may therefore be recycled, and used in the reactors. Optionally, the N-water is passed through a "mixer and heater", whereby it may act as both N-source, as heating feedstock within the reactor, and/or as a second diluting liquid to control the ratio of dry matter and/or the concentration and ratios of N-comprising components, such ammonium ($NH_4$), ammonia ($NH_3$) and nitrogen ($N_2$).

The gaseous part from the absorber NS2 that is not fixed in the NS-fertilizer may be emitted to the surroundings, optionally using a bio-filter.

Nitrogen from the solid degasified biomass may also be extracted via the N-stripping in the NS1 and NS2 units. Degasified biomass from the screw press may be subjected to a separation step, indicated as "band sieve" in FIG. 1, and the resulting volatile nitrogen containing compounds are subsequently absorbed and fixed in the NS1 and/or NS2 units.

To improve the efficiency of the process, the N-steamer may utilise the warm and moist steam comprising N from a dryer unit (such as a drum or band dryer). Drying units are common features of any system for treating and/or producing biomass, and is used for treating or pretreating the biomass to a desired moisture content, which is suitable for the product (e.g. dry fibers) or the process steps to be carried out (e.g. incineration). For example drying units may be used for pretreating or treating biomass such as straw that has been exposed to rain, and agricultural waste such as manure, which has a high moisture content. Stand-alone drying units typically emit the exhaust gas to the surroundings. The exhaust gas from a drying unit for biomass typically contain warm and moist steam comprising nitrogen (N), e.g. in the form of ammonia ($NH_3$), which originates from the biomass. Direct emission to the surroundings may be disadvantageous for both the environment and the work place conditions due to the N-components and associated smells. To minimise the adverse impact of the exhaust gas on the surroundings, the exhaust gas may be cleaned by a filter, e.g. a bio-filter, or collected in N-stripping units. Alternatively, the drying unit may be combined with a N-steamer as shown in FIG. 1, whereby the exhaust gas from the drying unit is utilised and cleaned within the N-steamer.

Biomass fermentation includes drying of the biomass. Drying of large quantities are advantageously carried using a drum or band dryer, however any drying means may be utilised. Drying may be carried out between any steps of the processes shown in FIG. 1, e.g. after fermentation in the biogas reactors. The drying results in the production of ammonia, or warm and moist steam comprising nitrogen (N). Thus, the exhaust gas from a dryer, such as the drum or band dryer in FIG. 1, will comprise nitrogen in the gaseous phase.

Figure 8:
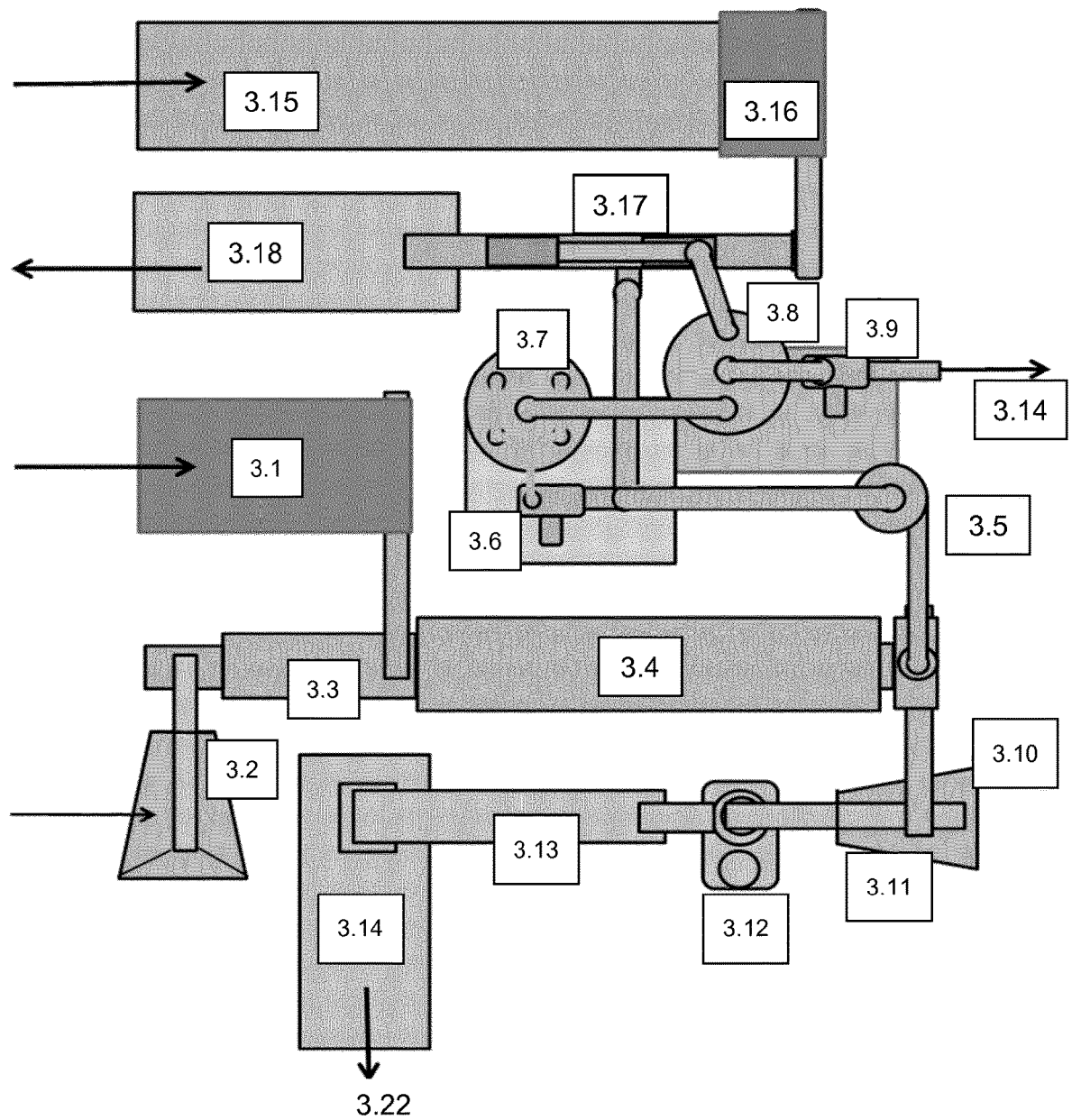
FIG. 8 shows an embodiment of a system for treating biomass comprising a continuously operating N-steamer 3.17, where the N-steamer is integrated and used for filtering and/or cleaning of steam/fluegas from a drying unit, in combination with production of biogas substrates. The Figure is further described in Example 3.

Conventionally, N-steam from a biomass dryer may be collected in one or more NS-units, i.e. N-stripping and sanitation units. Alternatively, or additionally, the warm and moist N-steam can be diverted to an "N-steamer", as shown in FIG. 8 and further described in Example 3.

The N-steamer utilises the warm and moist steam comprising N from the dryer to treat or pre-treat materials such as complex waste, complex agricultural waste, and some category II waste, including crop residues, straw, grass and the like. By this treatment, effectively ammonia treatment, the materials will be rendered usable as i) valuable biomasses for biogas production, as ii) fibre material for adding to the fibrous solid substrate in pellet form, as iii) a substrate directly utilisable for cultivating fungal cells and/or spores, or iv) a substrate directly utilisable as animal feed.

Communication Between Dryer and N-Steamer

After fermentation in the biogas reactor, the solid fibers are advantageously dried as illustrated in FIG. 1. Furthermore, for the production of ready to use substrates and pellets, it is essential that the biomass or fibers for the pellets are dry, since moisture may affect the shaping of the pellets as well as the shelf life of the produced pellets.

Thus before pellet pressing, the biomass or fibers used for the pellets may be dried. The drying may be carried out in any heat treatment means, and for large quantities it may be advantageous to use a drum dryer or band dryer. The biomass fibers are introduced into the dryer either directly from a grinder or it may be degasified biomass from a reactor as indicated in FIG. 1.

The drying process results in the formation of a warm and moist steam comprising nitrogen (N). To improve the energy efficiency of the system shown in FIG. 1, the warm and moist N-steam from the dryer may be diverted to the N-steamer (and/or NS1). In the N-steamer, the steam is then used for ammonia pretreating the N-steamer feedstock. Thus, in an embodiment of the invention, the N-steamer is in fluid communication with a dryer unit.

The same N-steamer feedstock as exemplified for FIG. 1 may be used when the ammonia pretreatment is carried out with N-steam from a dryer. Thus, the N-steamer feedstock may be a complex waste such as straw, grass and the like, which has first been cut and/or grinded to a desired length.

N-Steamer or Gas-Steamer

The efficiency of the gas or ammonia pretreatment may be evaluated by the required treatment time, or retention time. By the term "retention time" is meant the amount of time between introducing and removing the biomass from the N-steamer, that is required for sufficient and complete pretreatment. Thus the retention time directly determines the quantities of biomass that can be treated over a given time.

The retention time will generally depend on the contact degree and intensity, and how the contact between the biomass and the gas or steam comprising nitrogen is facilitated.

An embodiment of the invention relates to a system for treating biomass with steam comprising nitrogen, said system comprising: at least one conduit comprising: at least one biomass inlet and at least one biomass outlet, at least one steam inlet and at least one steam outlet, and said system further comprising: a transport unit configured to move the biomass through the conduit from the at least one biomass inlet to the at least one biomass outlet thereby defining a biomass transport direction, and wherein the system is configured such that steam flowing from the at least one steam inlet to the at least one steam outlet crosses the biomass transport direction.

More specifically, the retention time will depend on adjustable, operational factors such as temperature, pH, N concentration, moisture content of the biomass, and relative humidity of the atmosphere for treatment. The retention time may also depend on the compaction degree, or density or porosity, of the biomass feedstock to be treated. For example, if the feedstock is densely compacted, there will be parts of the feedstock that has little or no direct contact to the N-steam, i.e. the N-steam will have little or no direct access to the surface of the feedstock. Longer retention times will therefore be needed in these cases for sufficient ammonia treatment of the complete feedstock. On the other hand, if the feedstock is not compacted, all parts of the feedstock may have similar contact to the N-steam; however the quantities of feedstock to be treated over a given time may be smaller for the case with non- or low-compacted feedstock.

The compaction degree, and thus the surface area of the feedstock exposed to the ammonia treatment, will depend on the size of the fibers. The size and surface area of the fibers may be adjusted in the cutter as shown in FIG. 1.

The compaction degree will also depend on how the feedstock is introduced into and removed out of the N-steamer. For example if the feedstock is piled within the N-steamer under the force of gravity, the compaction degree will be lower than if the feedstock is piled under a load. Further, the higher the load, the higher the compaction degree.

Figure 2A:
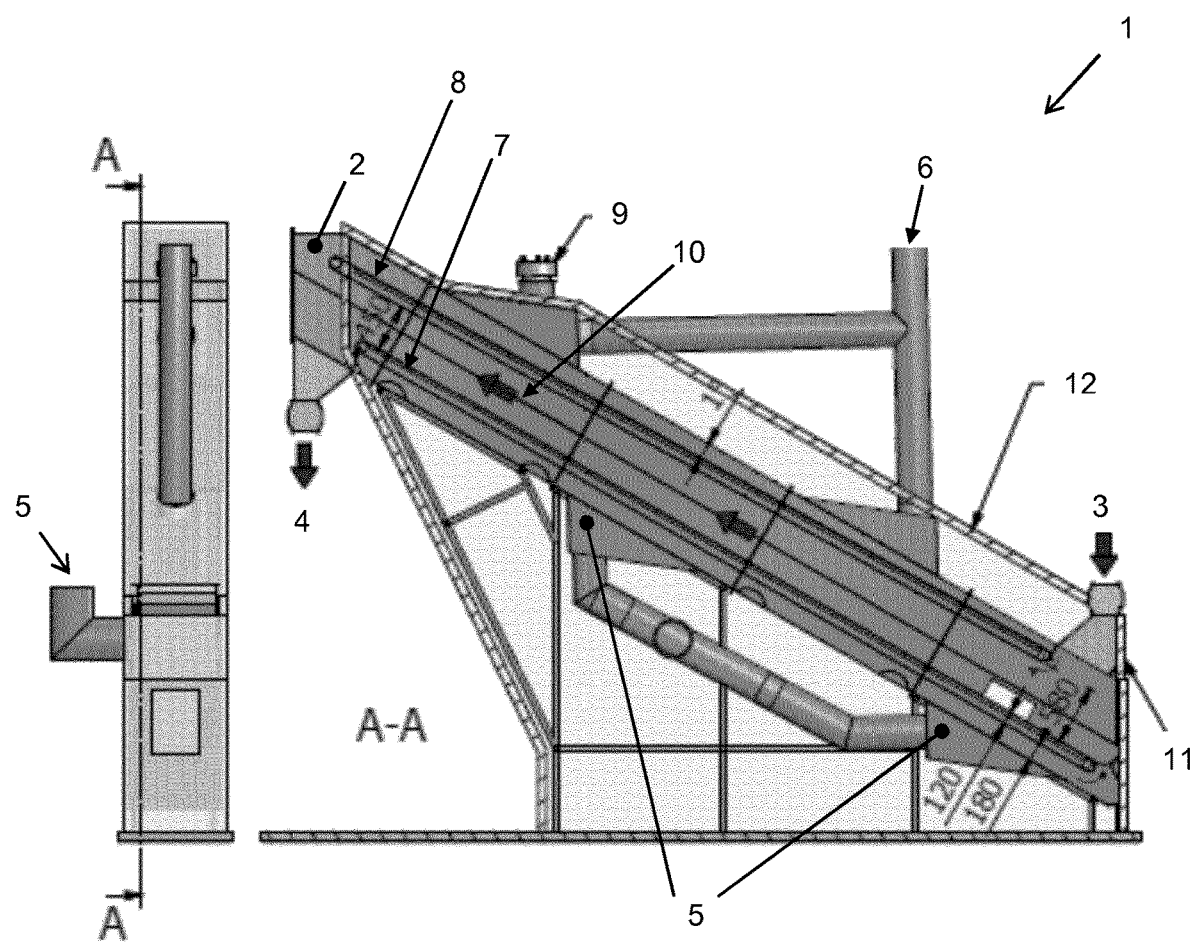
FIG. 2A shows an embodiment of the disclosure, where a N-steamer 1 is configured to operate continuously. A cross-sectional view along the longitudinal dimension of the N-steamer is shown to the right in FIG. 2A, and a side or end view A-A, i.e. showing the shorter dimension of the N-steamer, as seen from the lower end where the biomass is introduced, is shown to the left of FIG. 2A. Examples of dimensions in millimeters are included. The reference numbers refer to: the N-steamer system 1, conduit 2, biomass inlet 3, biomass outlet 4, steam inlet 5, steam outlet 6, transport unit 7,8 exemplified as a first conveyor belt 7 and a second conveyor belt 8, safety valve 9, biomass transport direction 10, moisterising means 11, insulation 12.
Figure 2B:
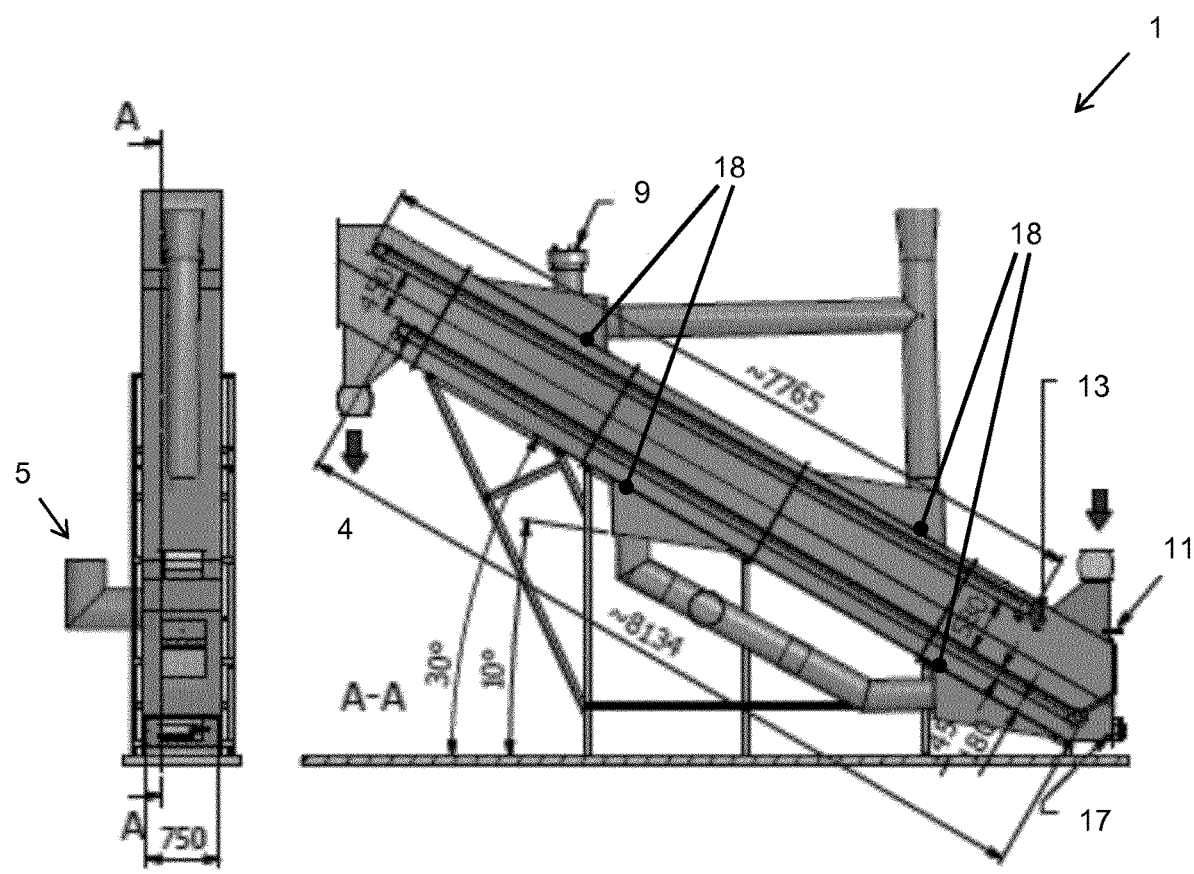
FIG. 2B shows an embodiment of the disclosure, where a N-steamer 1 is configured to operate continuously. A cross-sectional view and an end view A-A, similar to FIG. 2A, is shown, and examples of dimensions in millimetres and angles are included. The embodiment shown in FIG. 2B includes the same features as FIG. 2A, and in addition comprises distribution means 13, one or more water collector(s) 17, and sensors 18 for measuring nitrogen (N) and/or ammonia ($NH_3$) concentration, relative humidity, and/or temperature.
Figure 2C:
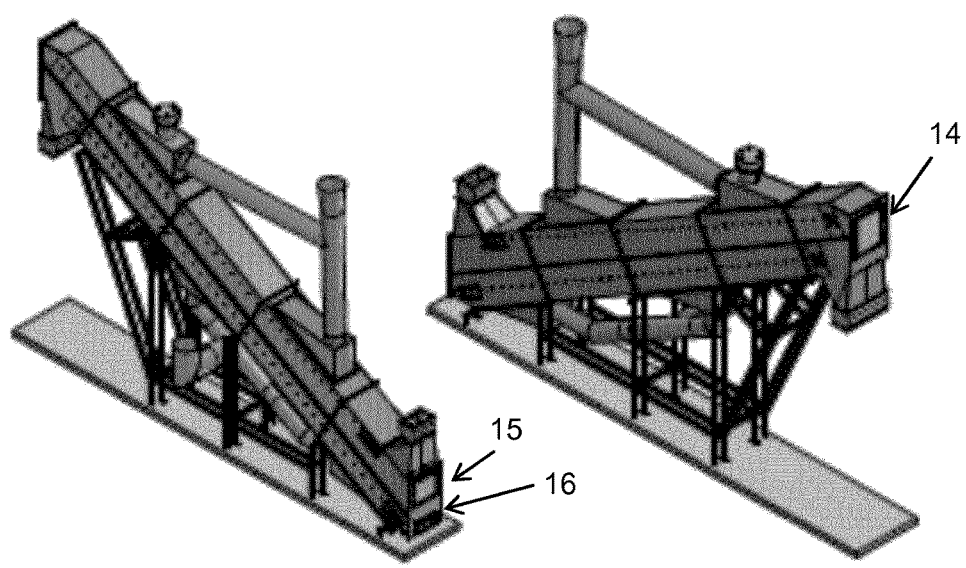
FIG. 2C shows embodiments of the disclosure, where the N-steamer is seen in perspective view from respectively the lower end (left), and higher end (right). The embodiments may include the same features as in FIGS. 2A-B, and in addition shows detachably attached gables at both ends 14,15, and a trapdoor 16.

The efficiency, or the quantities of biomass that can be treated over a given time, may also be improved in a continuous N-steamer process in contrast to a batch process. FIGS. 2A-C show embodiments of a N-steamer configured to be operated continuously. A cross-sectional view along the longitudinal dimension of the N-steamer is shown to the right in FIGS. 2A-B, and a side view A-A as seen from one of the lower end, i.e. the shorter dimension of the N-steamer, is shown to the left of FIGS. 2A-B.

The N-steamer system comprises a conduit 2, where the biomass enters through the biomass inlet 3 and exits through the biomass outlet 4, and where the biomass is moved continuously through the conduit from the biomass inlet to the biomass outlet by a transport unit 7,8, thereby defining a biomass transport direction 10. Evidently, larger amounts or quantities of biomass may be treated within the N-steamer if the biomass transport direction is within the longitudinal direction of the conduit. Thus, in an embodiment of the invention, the biomass transport direction is along the longitudinal direction of the conduit.

In addition to moving the biomass along the biomass transport direction, the transport unit may be configured to control the compaction degree of the biomass, and further to control the compaction degree of the biomass along the biomass transport direction. The biomass compaction degree within a unit, such as the N-steamer, may be controlled and adjusted by a spacial restriction. Thus under otherwise similar conditions, biomass transported along a conduit with a lower cross-sectional area will be more compacted than biomass transported along a conduit with a bigger cross-section area.

In an embodiment of the invention, the transport unit is configured to control the compaction degree of the biomass. In a further embodiment, the transport unit is configured to control the compaction degree of the biomass along the longitudinal direction of the conduit. In a further embodiment, the transport unit is configured to control the compaction degree of the biomass by the cross-sectional area of the conduit.

Inherently due to the N-steam treatment, biomass entering the N-steamer will have a lower compaction degree than the biomass exiting the N-steamer. The steam treatment including wetting and moisturising of the biomass, e.g. straws, will cause the straws to collapse and compact. Thus, the term increased "compaction degree" reflects both the increase in density of the biomass material (in $kg/m^3$), as well as the decrease in air between the material fibers (i.e. increased bulk density in $kg/m^3$). Advantageously the transport unit is configured to accommodate the inherent change in compaction degree along the conduit or biomass transport direction. For example, the transport unit may accommodate an increase in biomass density and closer packing by adjusting the spatial restriction. Typically, the biomass entering the conduit has advantageously a biomass compaction degree corresponding to a biomass density of 200-250 $kg/m^3$, which includes a typical moisture content of ca. 30%. At the conduit exit, the moisture content within the biomass has typically increased to typically 50%, corresponding to a biomass density of 250-300 $kg/m^3$. In an embodiment of the invention, the transport unit is configured to adapt to the compaction degree of the biomass. In a further embodiment of the invention, the transport unit is configured to adapt to the compaction degree of the biomass along the longitudinal direction of the conduit. In a further embodiment, the transport unit is configured to adapt to a change in the compaction degree of the biomass by adjusting the cross-sectional area of the conduit. In a further embodiment, the transport unit is configured to adapt to a change in compaction degree of the biomass ranging from 200-250 $kg/m^3$ to 250-300 $kg/m^3$.

The spatial restriction of the transport unit to control the biomass compaction degree may have any form. For example, the transport unit may comprise of two or more transport planes configured to sandwich the biomass in-between them. The biomass is then transported within the transport unit by the transport planes being synchronised and operated in the same transport direction and with compatible transport speeds. In an embodiment of the invention, the transport unit comprises two or more transport planes configured to sandwich the biomass in-between said planes. In a further embodiment, the two or more transport planes are configured to be synchronised and operated in the same transport direction 10 and with the same transport speed.

The spatial restriction, or the biomass compaction degree, within a transport unit comprising transport planes may be controlled by the distance(s) between the transport planes, and the change in the distance(s) between the transport planes along the conduit. Advantageously, the distance(s) between the transport planes decrease along the conduit, or the biomass transport direction, due to the inherent compaction of the biomass along the conduit. Advantageously, the distance(s) between the transport planes decrease in a linear, exponential, and/or logarithmic way. For a linearly decreasing distance between transport planes, the distance between the transport planes may be determined by the inclination ratio between the transport planes.

In an embodiment of the invention, the distance between the two or more transport planes is configured to control the compaction degree of the biomass. In a further embodiment, the distance(s) between the two or more transport planes decrease along the biomass transport direction. In a further embodiment, the distance(s) between the two or more transport planes is controlled by an inclination ratio between the transport planes.

The distance(s) between the transport planes may easily be controlled manually or automatically by use of a sensor. In an embodiment of the invention, the distance(s) between the two or more transport planes are controlled by a sensor.

In FIG. 2 the transport unit is exemplified as two conveyor belts 7,8, wherein the first conveyor belt 7 defines a lower transport plane, and the second conveyor 8 belt defines a second and upper transport plane. The compaction degree and retention time of the biomass being treated in the N-steamer of FIG. 2 will depend on the conveyor belts, i.e. the transport direction 10 and transport speed of the planes, as well as the inclination of the planes and the distance between the planes.

A transport unit in the form of two conveyor belts has the advantages of being simple and easy to operate and maintain. For example, the compaction degree of the biomass along the biomass transport direction is easily controlled by the inclination of the conveyor belts.

In an embodiment of the invention, the transport unit comprises two or more conveyor belts. In a further embodiment, the transport unit comprises two conveyor belts, wherein the first conveyor belt defines a lower transport plane, and the second conveyor belt defines an upper transport plane. In a further embodiment, the inclination of the first conveyor belt 7 is below 85 degrees, more preferably below 70, 60, 50 or 40 degrees, and most preferably below 30 degrees, such as 20 degrees. In a further embodiment, the inclination of the second conveyor belt 8 is equal to or below the inclination of the first conveyor belt 7.

Examples of dimensions of the transport unit and the N-steamer are included in FIG. 2. In an embodiment of the invention, the distance between the first and second conveyor belts, i.e. the distance between the two planes defined by the lower and upper conveyor belt, decreases from 580 mm at the inlet, to is 450 mm at the outlet.

The conveyor belts may be of any material compatible with the biomass and resistant enough to the ammonia steam, and the dimensions of the conveyor belt may be any dimensions compatible with the at least one conduit. In the embodiment exemplified in FIG. 2, the pulleys, or drums, which move the loop of the lower conveyor belt, are configured to a distance of 120 mm between the upper and lower loop of the belt. The upper loop of the belt is further placed at a distance of 180 mm from the nearest surface of the conduit. The upper conveyor belt is placed at a distance from the surface of the conduit which varies. From FIG. 2 it is seen that the distance between the upper conveyor belt and the nearest surface of the conduit increases from the inlet to the outlet.

The biomass entering the N-steamer may have any compaction degree depending on the size and how the biomass is dosed to the N-steamer. To ensure a consistent compaction degree, it may be advantageous that the biomass is fed to the biomass inlet via distribution means 13. The distribution means will thus ensure an even distribution of the biomass across the height and/or width of the conduit. Examples of distribution means may be any automated feed and dosage equipment, including screw conveyors. A screw conveyor may ensure even distribution by rejecting pieces of biomass that do not fit inside the conduit or are have unsuitable sizes or forms. An example of a N-steamer comprising distribution means in the form of a screw conveyor 13 is shown in FIG. 2B. The distribution means may further ensure that suitable dosage rates of biomass is fed to the continuously operating N-steamer by suitable regulation means, as e.g. the rate of the screw conveyor. In an embodiment of the invention, the system further comprises biomass distribution means, such as automated feed and dosage equipment and/or a screw conveyor.

The efficiency of the gas or N-steam treatment is dependent on the contact degree between the steam flow and the biomass. The better the contact and the better the contact is distributed within the conduit, the more efficient the treatment. It is therefore advantageous that the gas/steam flow is distributed within the at least one conduit, and further is distributed within the volume of biomass placed at the transport unit 7,8.

A distribution of the gas/steam flow within the biomass volume may be obtained by a transport unit comprising multiple openings for steam inlet and -outlet. For example, the conveyor belts 7, 8 exemplified in FIG. 2B may comprise multiple openings, holes, or perforations placed along the length and width of each belt, whereby gas/steam placed in the conduit 2, such as gas/steam entering the conduit from the inlet 5 or gas/steam exiting the conduit at the outlet 6, have multiple direct contact points with the biomass.

Figure 12:
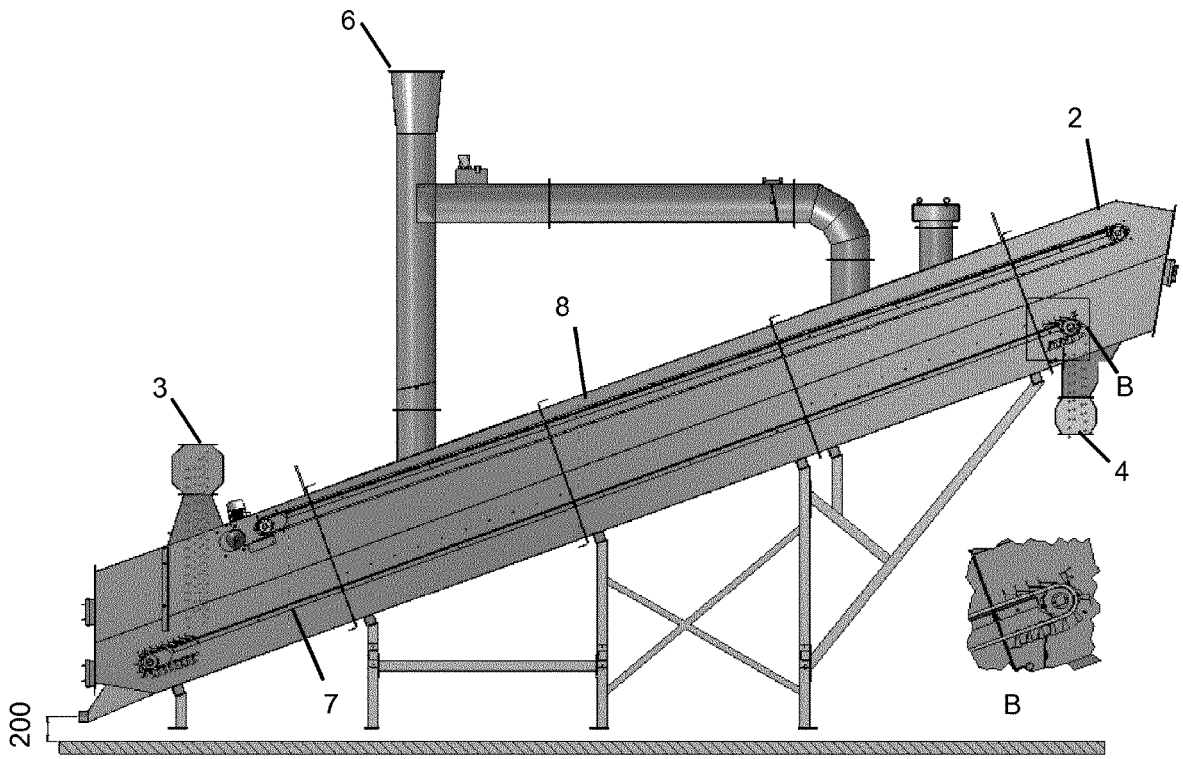
FIG. 12 shows an embodiment of the disclosure, where the first conveyor belt 7, which defines a lower transport plane, comprises multiple openings 19 for gas/steam inlet and -outlet. Examples of dimensions are included.

FIG. 12 shows an embodiment, where the first conveyor belt 7, which defines a lower transport plane, comprises multiple openings 19 for gas/steam inlet and -outlet. In a further embodiment, the multiple openings are obtained by the first conveyor belt comprising multiple planar sections. The multiple planar sections are for example shown in the part of the conveyor belt near the biomass outlet 4, also marked as "B" in FIG. 12. An enlarged image of the area B is further shown in FIG. 13.

Figure 13:
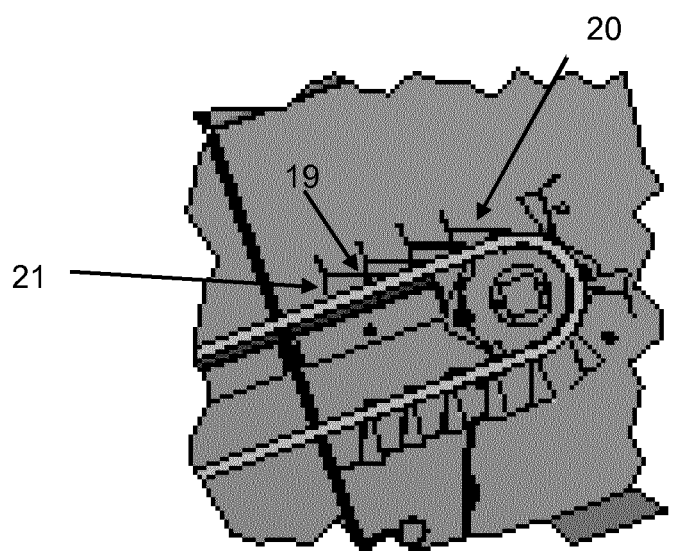
FIG. 13 is an enlargement of the area indicated as "B" in the embodiment of FIG. 12, where the multiple openings of the conveyor belt is further detailed.

As further seen in FIG. 13, the first conveyor belt comprises multiple planer sections 20, where each planer section is configured to be angular displaced relative to the transport plane, such that each planar section forms an angle to the transport direction of the transport plane. The angular displacement is seen to results in the formation of an opening 19 between neighboring planar sections. Preferably, the angular displacement is below 45 degrees, more preferably below 30, 20, 10 degrees.

In addition to the openings 19 between neighboring planar sections, the angular displaced planar sections has the advantage that the amount of biomass that is dropped or wasted from the transport unit is reduced, since the openings of the conveyor belt are not in direct contact with the biomass.

In an embodiment of the disclosure, the transport unit comprises multiple openings for gas/steam inlet and -outlet. In a preferred embodiment, the first conveyor belt 7 defining the lower transport plane, comprises multiple openings for gas/steam inlet and -outlet.

In an embodiment of the disclosure, the first conveyor belt comprises multiple planar sections, wherein each planar section is angular displaced relative to the transport plane. In a further embodiment, the angular displacement is below 45 degrees, more preferably below 30, 20, 10 degrees.

The angular displacement may be obtained by a support element 21, such as a supporting leg or supporting plate, placed opposite the transport direction of the planar section, such as along the edge of the planar section opposite the transport direction. FIG. 13 shows an embodiment, where the support element is a supporting plate. Advantageously, the support element further acts as securing means for securing or fixing the biomass to the transport plane. This may be obtained by the support element extending beyond the planar section, and into the volume of the transported biomass. For example, the support element may be a support plate, placed orthogonal and symmetrical to the planar section, at the edge of the planar section opposite to the transport direction, as illustrated in FIG. 13.

In an embodiment of the disclosure, each planar section comprises a support element 21 placed opposite the transport direction. In a further embodiment, the support element is configured to act as securing means for the biomass. In a further embodiment, the support element is a plate, placed orthogonal and symmetrical to the planar section at the edge of the planar section opposite to the transport direction.

FIGS. 12-13 show an embodiment, where the planar sections are further fixed to the conveyor by hinge means. The hinge means are placed at the edge of planar section facing the transport direction, i.e. the opposite edge as the support element. Thus, at the end of the conveyor (indicated by "B") in FIG. 12, the planar sections are rotated around the hinge, thereby facilitating the dropping of biomass from the conveyor belt and the planar section.

In an embodiment of the disclosure, the planar sections are fixated by hinge means. In a further embodiment, the hinge means are placed at the edge of the planar section facing the transport direction.

Gas-Steamer or N-Steamer Atmosphere

The biomass retained within the conduit of the gas-steamer/N-steamer is exposed to a gas/steam flow which enters the conduit at the steam inlet 5 and exits the conduit at the gas/steam outlet 6, as illustrated in FIG. 2. The biomass is exposed to the gas/steam, due to the flow path of the gas/steam crosses the biomass transport direction as the gas/steam flows from the at least one gas/steam inlet to the at least one gas/steam outlet.

The efficiency of the gas/N-steam treatment is dependent on the contact degree between the gas/steam flow and the biomass. The better the contact and the better the contact is distributed within the conduit, the more efficient the treatment. It is therefore advantageous that the gas/steam flow is distributed within the at least one conduit. A distribution of the gas/steam flow may be obtained by including multiple gas/steam inlets and -outlets, and where the gas/steam inlet and -outlets are placed at different distances along the conduit or biomass transport direction.

In an embodiment, the system comprises two or more gas/steam inlets 5, and two or more gas/steam outlets 6. In a further embodiment, at least one gas/steam inlet and at least one gas/steam outlet is placed upstream the biomass transport direction, and at least one gas/steam inlet and at least one gas/steam outlet is placed downstream the biomass transport direction.

The efficiency of the gas/N-steam treatment will also depend on the concentration of the gas/N-steam the biomass is be exposed to. For example, after reaction with biomass, the nitrogen concentration of the N-steam will be lower. Thus, used N-steam will be less efficient for a treatment. It is therefore advantageous that the N-steam is replaced quickly, or exits the conduit quickly after contact with the biomass, as it will be used. This may be obtained by placing a gas/steam inlet adjacent to a gas/steam outlet.

Biomass entering the at least one conduit will furthermore require more treatment than biomass near the exit of the conduit, which has been exposed to the gas/steam along the conduit. It may therefore be advantageous that a gas/steam inlet and/or a gas/steam outlet is placed near or adjacent to the biomass inlet. FIG. 2 shows an embodiment, where the at least one conduit comprises two gas/steam inlets and two ga/steam outlets. One gas/steam inlet and -outlet is placed adjacent to the biomass inlet, and one gas/steam inlet and -outlet is placed adjacent to the biomass outlet.

In an embodiment of the invention, the at least one gas/steam inlet 5 and the at least one gas/steam outlet 6 are placed at opposite sides of the at least one conduit 2, such that the gas/steam flows across the longitudinal direction of the conduit 2. In a further embodiment, the at least one gas/steam inlet and at least one gas/steam outlet are placed adjacent to the biomass inlet 3, and at least one gas/steam inlet and/or at least one gas/steam outlet are placed adjacent to the biomass outlet 4.

Advantageously the gas/steam comprises nitrogen, whereby it facilitates ammonia pretreatment of the biomass within the conduit. Further advantageously the nitrogen comprising steam/gas is recycled steam/gas from a drying unit as illustrated in FIG. 1. By recycling gas/N steam from a drying unit, the nitrogen emission from a biomass system may be controlled and reduced. Thus, the system of the invention provides a more environmental friendly method for processing biomass. In addition to controlling and minimizing the nitrogen emission to the environment, the method and system described may also provide the benefit of improving the workplace health and safety conditions.

Thus, the system comprising the fluidly connected N-steamer and drying unit may be implemented in different systems. Examples of different systems implementing the fluidly combined N-steamer and drying unit are further described in Examples 1-4.

In an embodiment of the invention, the system comprises a dryer 13 for drying biomass. In a further embodiment, the dryer and the N-steamer unit is fluidly connected. In a further embodiment, the gas exhaust from the dryer is connected to the at least one steam inlet 5.

The emission of nitrogen comprising steam from a system may further be controlled and reduced, by reducing any leakage originating from leaks in the conduit. Leakage from the conduit is found to be reduced and better controlled, when the gas/steam flows through the conduit at a negative pressure. This may be obtained by sucking the gas/steam at a higher flow rate at the gas/steam outlet 6 compared to the gas/steam inlet 5.

In an embodiment of the invention, the system is configured such that the gas/steam is sucked from the at least one gas/steam inlet 5 to the at least one gas/steam outlet 6 at a negative pressure.

To facilitate the negative pressure of the gas/steam, the at least one conduit must be configured to tolerate a certain negative pressure. For operational safety reasons, it is further advantageous that the system comprises regulation means to be activated if pressure goes outside the tolerated range. Thus, it may be advantageous that a safety valve is attached to the system, and fluidly connected to the at least one conduit. In an embodiment of the invention, the safety valve is a vacuum valve. In another and further embodiment, the safety valve is a VAM.

In an embodiment of the invention, the at least one conduit 2 is configured to tolerate a negative pressure of at least 0.1 bar, more preferably at least 0.2 or 0.3 bar. In another embodiment, the system further comprises a safety valve 9 configured to be activated at a negative pressure of 0.1, 0.2, or 0.3 bar.

For efficient ammonia pretreatment of biomass, the ammonia pretreatment is advantageously carried out at elevated temperatures, high moisture content, and/or neutral or weakly basic pH. The conditions may be obtained by using an N-steam, or steam comprising nitrogen, which has an elevated temperature, high moisture content, and/or neutral or weakly basic pH. A N-steam originating from a drying unit may comprise these properties.

In an embodiment of the invention, ammonia pretreatment is carried out using a N-steam with a temperature of about 60 to 95° C., such as 60-65° C., 65-70° C., 70-75° C., 75-80° C., 80-85° C., or 85-90° C.

In a further embodiment of the invention, ammonia pretreatment is carried out using a N-steam with a neutral or weakly basic pH. In a further embodiment, the pH is about 7 to 9 or 7 to 10, such as 7-7.5, 7.5-8, 8-8.5, 8.5-9, 9-9.5, or 9.5-10.

In a further embodiment of the invention, ammonia pretreatment is carried out using a N-steam with a moisture content of about 60 to 99%, such as 60-70%, 70-80%, 80-90%, 90-99%, and most preferably a moisture content above 90%.

The efficiency of the ammonia pretreatment may be further improved if the biomass to be treated is not complete dry. If the biomass contains some moisture, the wetting properties, or contact angle between the biomass and N-steam may be improved. Thus, it will be easier for the N-steam to contact and access the surface of the biomass to be treated. It may therefore be advantageous that the biomass entering the conduit contains some moisture. This may be obtained by placing moisturising means 11 near the inlet 3 of the biomass as illustrated in FIGS. 2A-B. Examples of moisturising means include humidifiers, such as water and/or steam humidifiers, where moisture in the form of steam and/or water is injected onto the biomass through a nozzle or a similar jacket with distribution manifolds.

In an embodiment of the invention, the system further comprises moisturising means 11 at the biomass inlet 3 for moisturising the biomass.

Particularly, biomass with a moisture content above 30% may be faster to treat with N-steam. Thus it is advantageous that the moisturising means are configured to moisturise the biomass to above 30%. In an embodiment of the invention, the ammonia pretreatment is carried out at biomass with a moisture content of about 30 to 50%, such as 30-35%, 35-40%, 40-45% or 45-50%.

To ensure sufficiently moisturised biomass, it may be advantageous to continuously inject more steam and/or water into the conduit than what is needed and can be absorbed by the biomass. A part of the excess water and/or excess condensed steam may be removed from the at least one conduit via one or more water collectors 17. The water collectors are advantageously placed at the lower end, and near the moisturising means as exemplified in FIG. 2B. In an embodiment of the invention, the system further comprises one or more water collectors 17.

The ammonia treatment within the at least one conduit may further be monitored and controlled by use of sensors. Advantageously the at least one conduit comprises one or more sensors 18 for measuring the temperature, relative humidity or moisture content of the gas/steam flow, and/or $NH_3$ and/or N-concentration of the gas flow. Based on the measured values, the temperature and contents of the gas/steam flow may be regulated.

The sensors may be placed at any point within the at least one conduit, and advantageously the sensors are placed at an inner surface of the conduit. Further advantageously, sensors are placed adjacent to the one or more steam inlet(s), and adjacent to the one or more steam outlet(s). Thus, by comparing the inlet values with the outlet values, the amount of heat, moist, and/or nitrogen (N) adsorbed and absorbed within the biomass may be calculated. In an embodiment of the invention, the system further comprises one or more sensors 18 for measuring the temperature, relative humidity, and/or $NH_3$ concentration of the steam, wherein the sensors preferably are placed adjacent to the steam inlet(s) and/or steam outlet(s).

Figure 14:
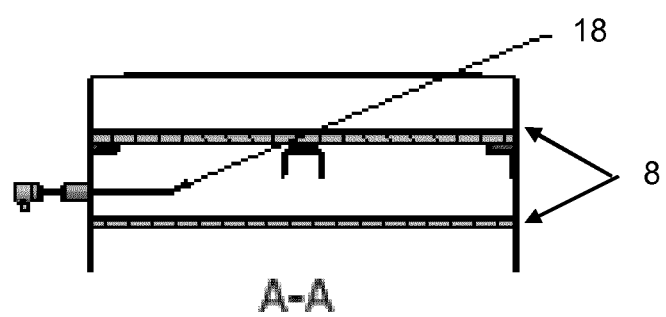
FIG. 14 shows an enlargement of the area indicated as "A-A" in the embodiment of FIG. 11, showing an embodiment of the position of the sensors, such as temperature sensors.

The efficiency of the gas/steam treatment will depend on the temperature of the biomass to be treated. Advantageously, one or more temperature sensors are placed adjacent to the transport unit, such as adjacent to the conveyor belt. Further advantageously, the temperature sensors are placed within a conveyor belt. As seen in FIG. 12, a conveyour belt consist of two pulleys or drums, around which the conveyor belt rotates. The conveyor belt thus defines a space between the pulleys, as illustrated in FIG. 14, which is an enlargement of the area indicated as A-A in FIG. 11. Thus, the temperature sensors are advantageously placed within the conveyor belt, i.e. within the space defined between the pulleys. For example, FIG. 14 shows an embodiment where the temperature sensor is placed within the second conveyor belt 8.

In an embodiment of the disclosure, one or more temperature sensor(s) are placed within a conveyor belt.

Figure 3A:
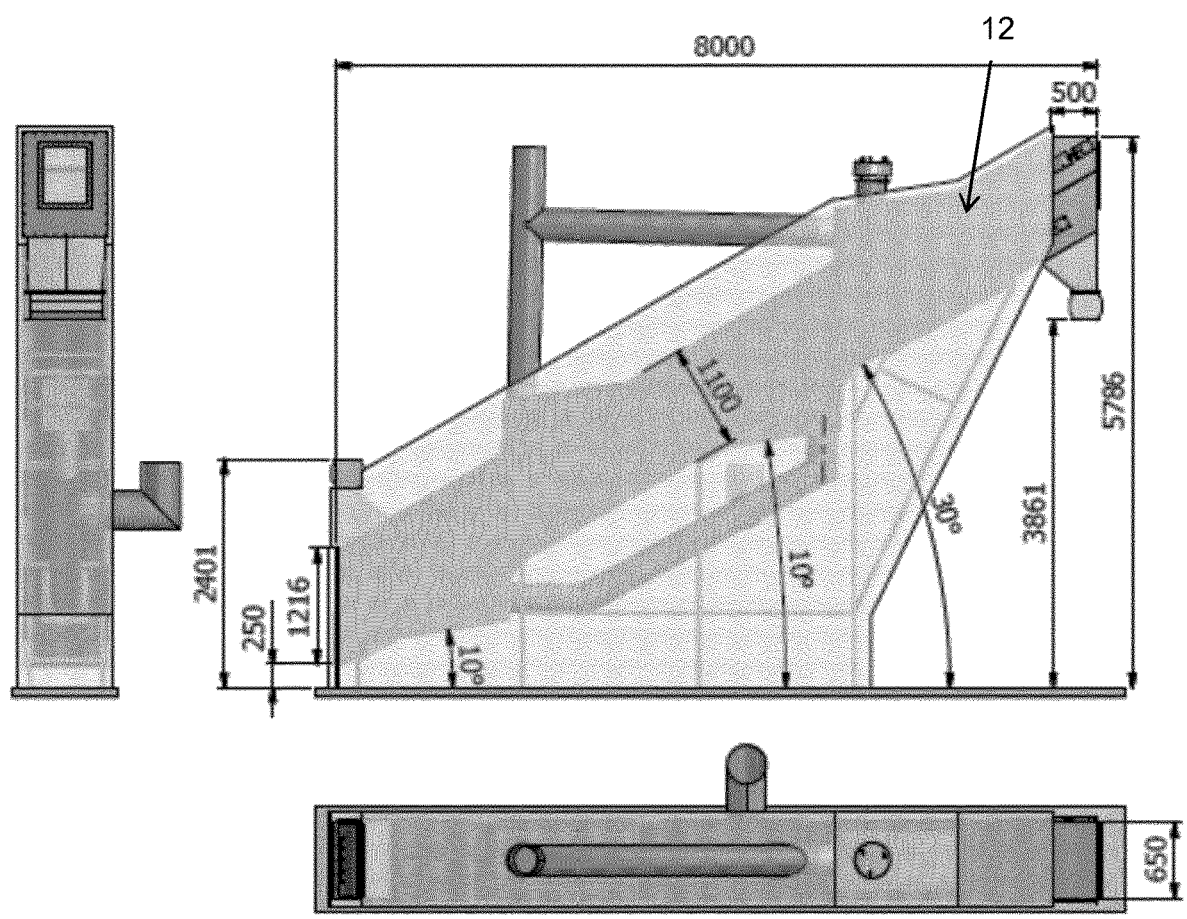
FIG. 3A shows an embodiment of the N-steamer of the disclosure, comprising an insulation layer 12, showing the N-steamer in a cross-sectional view along the longitudinal dimension of the N-steamer (main figure), and in addition an end view (left), and a top view (bottom). Examples of dimensions in millimetres and angles are included.
Figure 3B:
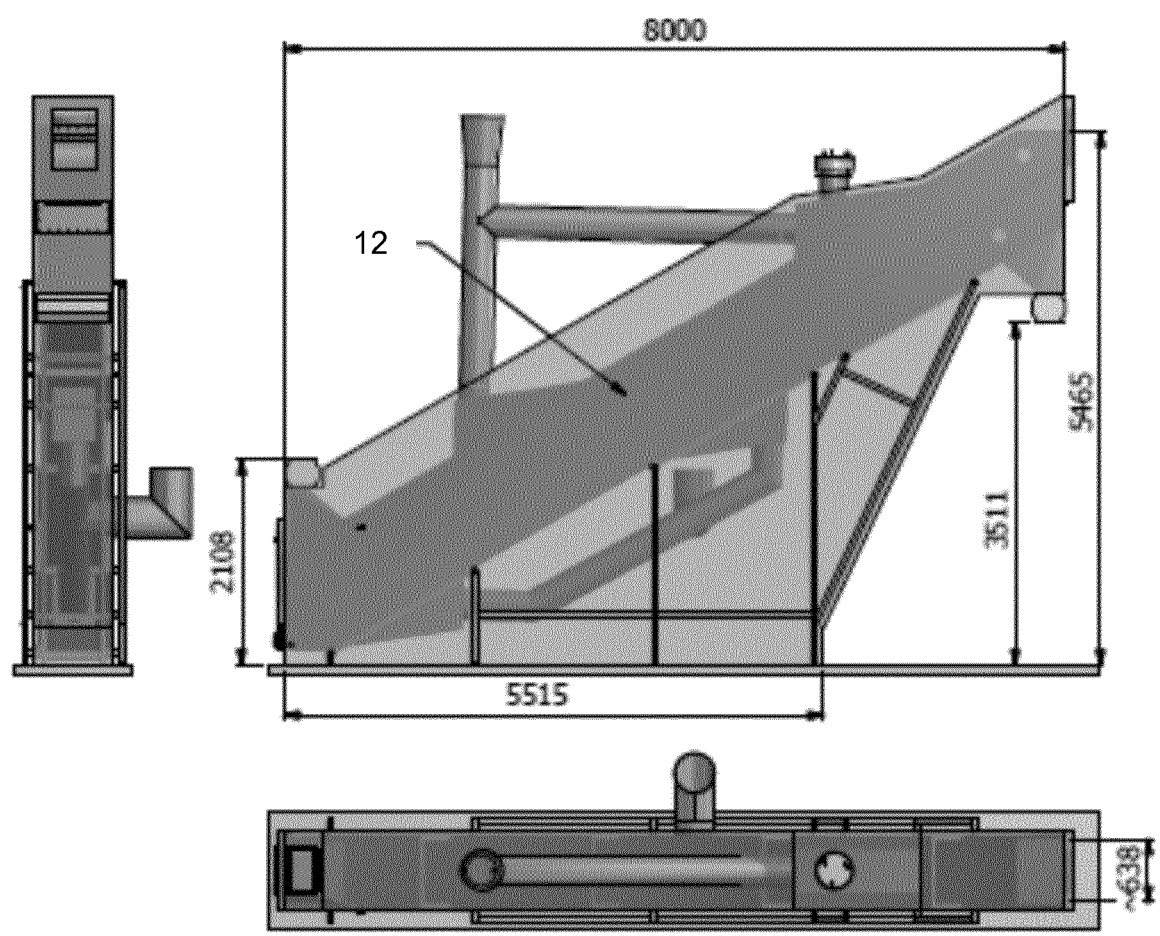
FIG. 3B shows an embodiment of the N-steamer of the disclosure, comprising insulation layer 12, showing the N-steamer in the same views as FIG. 3A. Examples of dimensions in millimeters are included.

To improve the energy efficiency of the system, it may be advantageous to insulate the system. FIG. 2A and FIGS. 3A-B show embodiments, where a layer of insulation 12 is encapsulating the N-steamer, i.e. the at least one conduit 2. For energy efficiency reasons, it may be advantageous that the manifolds comprising the N-steam entering the conduit is insulated too. Thus, in the embodiment illustrated in FIGS. 2-3, both the manifolds and the at least one conduit is encapsulated within the layer of insulation. It may further be advantageous that part of the optional dryer is insulated.

The insulation may have the additional benefit that the steam leakage from the conduit and manifolds are further reduced and controlled.

In an embodiment of the invention, the system comprises insulation means 12, wherein the insulation means encapsulate the at least one conduit 2 fully or partly.

In an embodiment of the invention, the insulation is of the type BALXTHERM. In a further embodiment, the insulation is a layer with a layer thickness between 150 to 10 mm, 100-50 mm, or 90-70 mm, and more preferably is about 80 mm.

FIG. 3 shows an embodiment of a N-steamer comprising an insulation layer 12. The Figure shows a cross-sectional view along the longitudinal dimension of the N-steamer (main figure), and in addition a side view (left), and a top view (bottom).

Figure 4A:
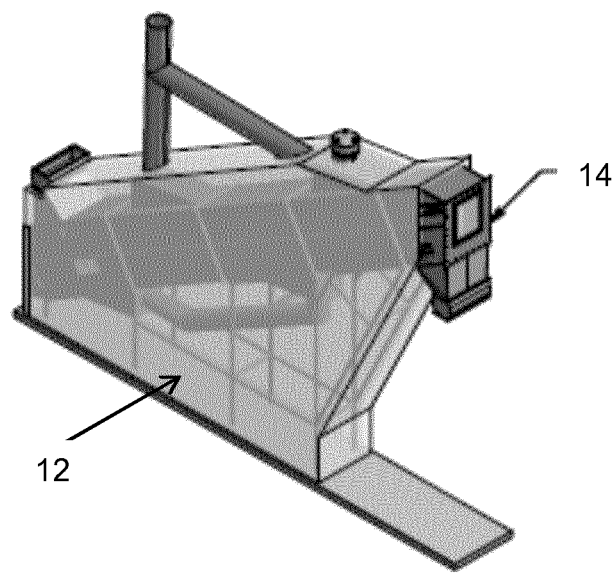
FIG. 4A-B show embodiments of the disclosure, where the N-steamer is seen in perspective view, and where the N-steamer is encapsulated in an insulation layer 12, and includes a detachably attached gable 14, placed near the biomass outlet, from which the N-steamer may be accessed for maintenance or inspection.
Figure 4B:
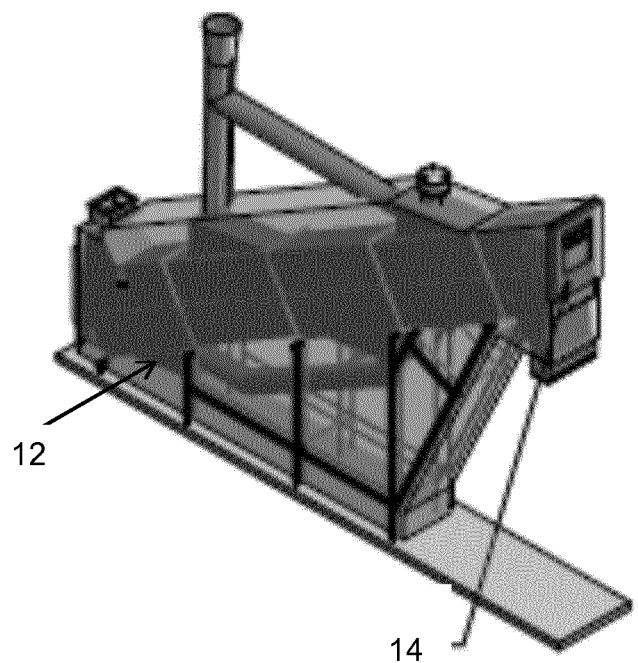
Figure 5A:
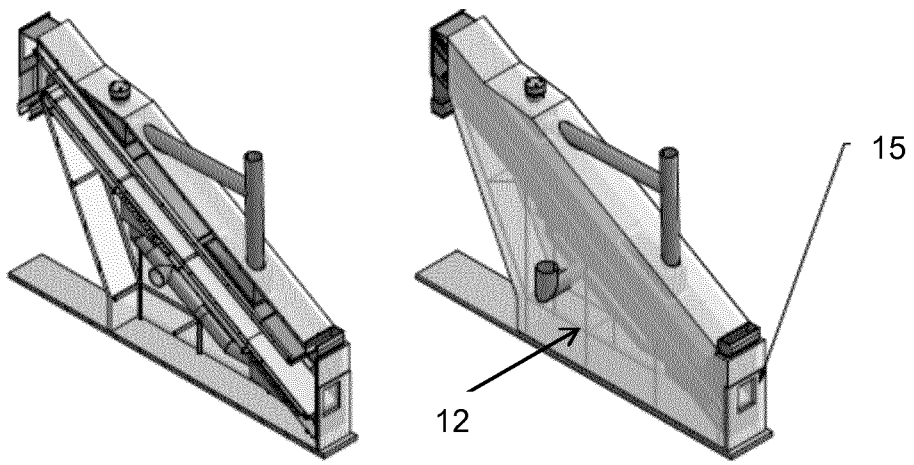
FIG. 5A shows embodiments of the disclosure, where the N-steamer is seen in perspective view, and where the N-steamer is respectively not encapsulated by an insulation layer (left), or encapsulated in an insulation layer 12 (right). The embodiments further include a detachably attached gable 15, placed near the biomass inlet, from which the N-steamer may be accessed for maintenance or inspection.
Figure 5B:
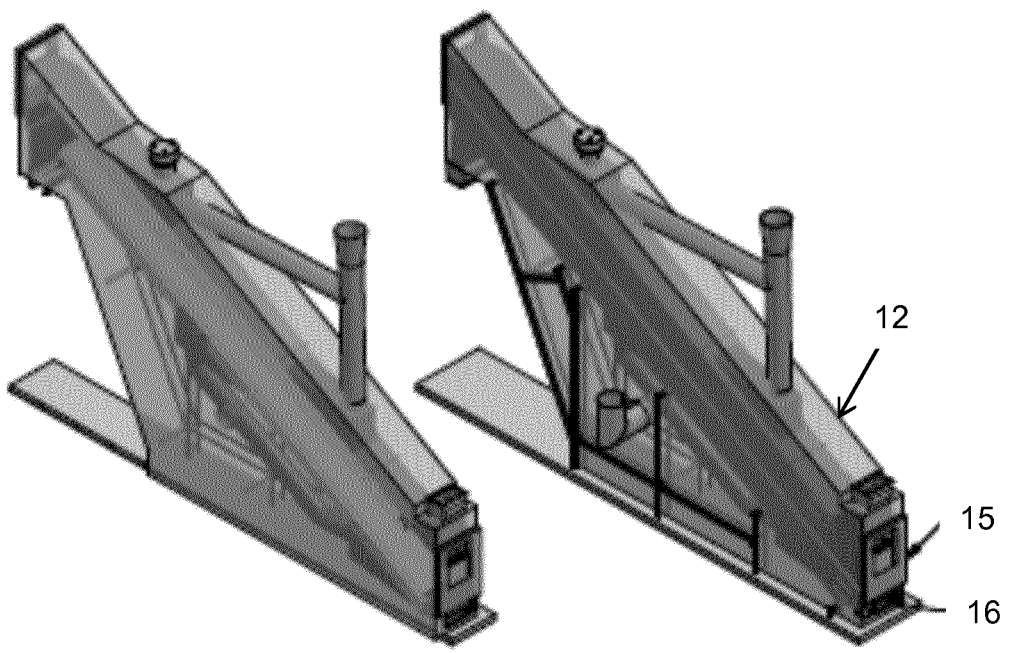
FIG. 5B shows embodiments of the disclosure, where the N-steamer is seen in perspective view, and where the N-steamer is encapsulated in an insulation layer 12, and includes a detachably attached gable 15, and a trapdoor 16, from which the N-steamer may be accessed for maintenance or inspection.

A perspective view of the N-steamer encapsulated in an insulation layer is shown in FIGS. 4-5. Advantageously, the interior of the N-steamer may be accessed from the outside for service and maintenance, without removing the entire insulation layer. FIG. 4 shows a detachably attached gable 14, placed near the outlet for biomass, from which the N-steamer may be accessed for maintenance. FIG. 5 shows a detachably attached gable 15, placed near the inlet for biomass, from which the N-steamer may be accessed for maintenance.

The distribution of the gas/steam within the conduit, and thus the efficiency of the gas/N-steam treatment, is also dependent on the position of the steam/gas inlets 5 and steam/gas outlets 6. Advantageous gas distribution may be obtained, when the gas/steam inlets are placed at the bottom side of the conduit, and the gas/steam outlets are placed at the top of the conduit, as illustrated in FIG. 2A.

Figure 11:
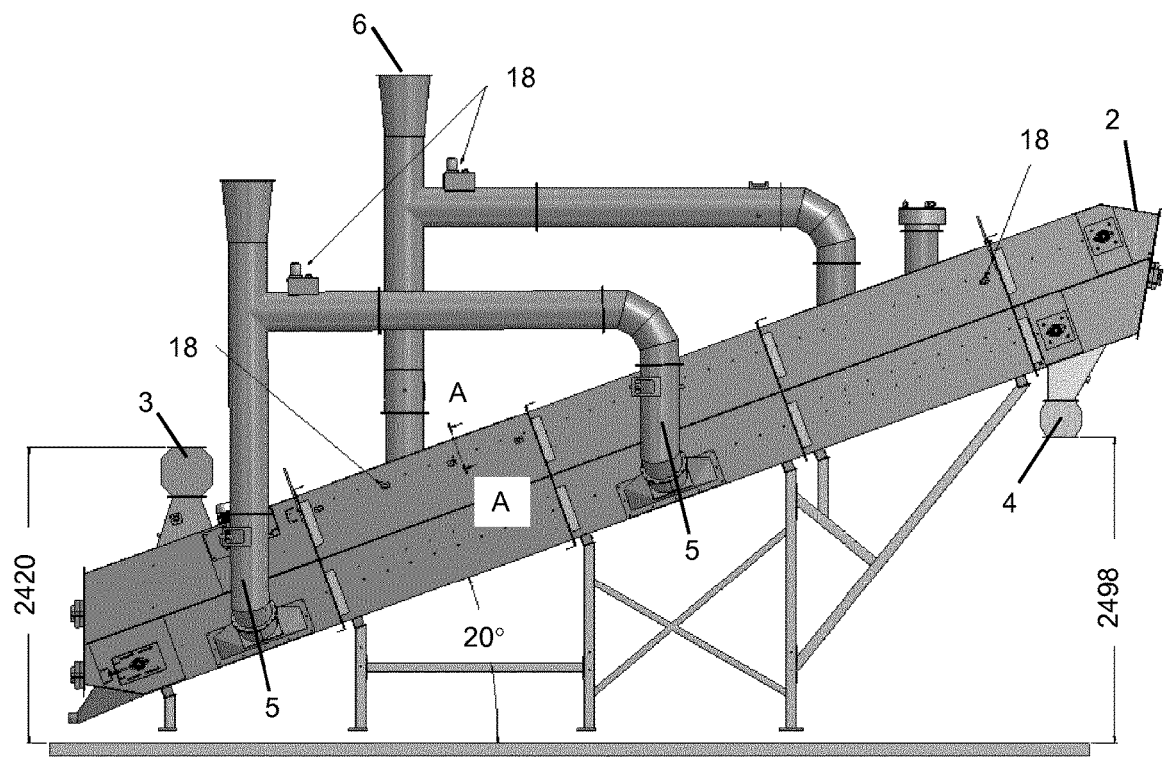
FIG. 11 shows an embodiment of the disclosure, where the gas/steam inlets and gas/steam outlets are placed at the longitudinal sides of the conduit. Examples of dimensions are included.

Alternatively, the steam/gas inlets and the steam/gas outlets are placed at the longitudinal sides of the conduit, as illustrated in FIG. 11. This position of the gas inlets and outlets further has the advantage that the amount of biomass that is dropped or wasted from the transport unit is reduced, due to the changed gas flow within the conduit and transport unit.

In an embodiment of the disclosure, the gas/steam inlets and gas/steam outlets are placed at the longitudinal sides of the conduit.

Operation

Efficient treatment of large quantities of biomass may be obtained by operating the system continuously. The system may be operated continuously with a continuous flow of gas/steam and a continuous flow of feed to the N-steamer (biomass feedstock), when the transport unit is operating continuously, for example in the form of a continuously operating conveyor belt.

In an embodiment of the invention, the transport unit is configured to be operated continuously.

The biomass retention time within the N-steamer may be controlled by the transport speed of the transport unit, for example the speed of a conveyor belt.

In an embodiment of the invention, the transport unit is configured to a biomass retention time within the at least one conduit 2 of between 5 minutes to 12 hours, more preferably between 10 to 60 minutes, and most preferably between 20 to 30 minutes.

The described system may be used for a method for treating biomass with steam comprising nitrogen (N), the method comprising the steps of:
 a) providing biomass 3,
 b) providing at least one conduit 2 comprising a flow of steam comprising nitrogen,
 c) introducing the biomass into a first end 3 of the at least one conduit 2,
 d) transporting the biomass along the conduit by transport means,
 e) removing the biomass from a second end 4 of the conduit 2,
 whereby the biomass is treated with steam comprising nitrogen.

To improve the contact degree between biomass and steam, it is advantageous that the flow of gas/steam is angled to the conduit, or the transport direction of the biomass.

In an embodiment of the invention, the flow of gas/steam is angled to the longitudinal direction of the conduit. In a further embodiment, the flow of gas/steam is essentially perpendicular to the longitudinal direction of the conduit.

The contact degree area and -angle between biomass and gas/steam may further be improved if the biomass is moist. Thus, in a further embodiment of the invention, the biomass of step (a) is further moisturised.

The embodiments of the N-steamer may be used for pretreating any type of biomass. Examples 1-2 describe two embodiments of possible use of the N-steamer. The embodiments of the N-steamer may further be used in combination with a biomass drying unit. Biomass drying units result in polluting exhaust gases, and the N-steamer may be used to clean the polluting exhaust gas from any drying unit. Examples 3-4 show two embodiments of the use of the N-steamer for cleaning exhaust gas comprising nitrogen. When a N-steamer and drying unit are combined, the energy efficiency of both systems may be improved.

To improve the energy efficiency of the system, and further to reduce detrimental nitrogen emissions to the environment, it is advantageous if the method is combined with a biomass drying step. It is further advantageous if the exhaust gas from the biomass drying step can be recycled.

In an embodiment of the invention, the biomass provided in step (a) has been dried in dryer. In a further embodiment, the exhaust gas from said dryer is introduced into the at least one conduit 2 and used as the steam flow provided in step (b).

For cost-efficiency the method may be carried out in a continuous manner by continuously supplying biomass and steam flow, wherein the steam flow optionally is a continuous flow from a continuously operated dryer. In an embodiment of the invention, the method is operated in a continuously manner.

The system of the present disclosure may also be applied as a drying unit or as a biofilter. For the system to be operated as a drying unit or biofilter, the steam inlet 5 and steam outlet 6 are operated as respectively gas inlet and gas outlet. Thus, instead of steam, the system may be used for any gas.

Advantageously, the gas is air, such that the steam inlet is an air inlet, and the steam outlet is an air outlet. Thus, the system may be operated as a drying unit, when biomass is treated with air.

Exhaust gasses may be cleaned by being exposed to biomass, since the biomass may absorb polluting elements. An example of an exhaust gas is the gas exiting the N-stripper (NS-2), as illustrated in FIG. 1. Thus, advantageously, the gas is an exhaust gas, such that the steam inlet is an exhaust gas inlet, and the steam outlet is an exhaust gas outlet. Thus, the system may be operated as a biofilter, when the biomass is treated with exhaust gas.

An embodiment of the disclosure relates to a system 1, said system comprising:
  at least one conduit 2 comprising:
    at least one biomass inlet 3 and at least one biomass outlet 4,
    at least one gas inlet 5 and at least one gas outlet 6, and
    a transport unit 7,8 configured to move the biomass through the conduit(s) from the at least one biomass inlet 3 to the at least one biomass outlet 4 thereby defining a biomass transport direction,
  wherein the system is configured such that gas flowing from the at least one gas inlet 5 to the at least one gas outlet 6 crosses the biomass transport direction.

In a further embodiment, the gas is steam. In another embodiment, the gas is air. In another embodiment, the gas is an exhaust gas.

An embodiment of the disclosure relates to a method for treating biomass with air, said method comprising the steps of:
  a) providing biomass,
  b) providing at least one conduit 2 comprising a flow of air,
  c) introducing the biomass into a first end 3 of the at least one conduit,
  d) transporting the biomass along the conduit by transport means 7,8,
  e) removing the biomass from a second end 4 of the conduit,
  whereby the biomass is treated with air.

Another embodiment of the disclosure relates to the use of the system a drying unit and/or a biofilter.

EXAMPLES

As described above, the system comprising the N-steamer, and optionally a fluidly connected N-steamer and drying unit, may be implemented in different systems for different purposes. The invention is further described by the examples provided below.

Example 1: System Comprising N-Steamer

Figure 6:
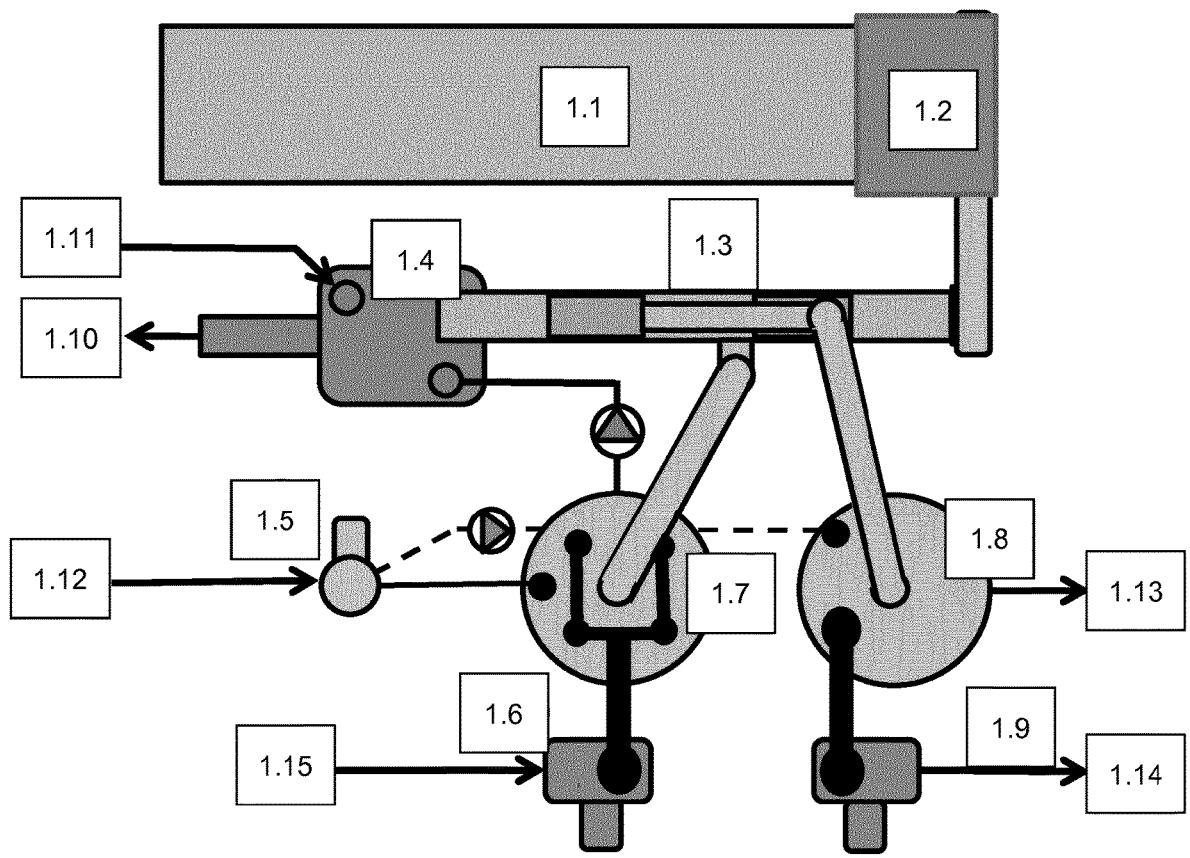
FIG. 6 shows an embodiment of a system for treating biomass comprising a continuously operating N-steamer 1.3. The Figure is further described in Example 1.

FIG. 6 shows an embodiment of a system for treating biomass comprising a continuously operating N-steamer 1.3. The steam comprising nitrogen used within the N-steamer may have any origin, and for example be N-steam from a drying unit (not shown in FIG. 6).

The biomass to be treated may be stored in a large container, such as a walking floor container 1.1, and fed in suitable dosage rates to the continuously operating N-steamer by regulation means, such as an automated feed and dosage equipment 1.2. An example of an automated feed and dosage equipment is a screw conveyor controlled by sensors. Such large storage containers may be particularly suitable for biomass in the form of straw.

Similar units and processing steps as shown in FIG. 1 may follow subsequent to the N-steamer. For example, the ammonia steam treated biomass may be used for producing biogas feedstock in a biogas reactor 1.10. To further improve the biomass feedstock for the biogas reactor, the N-steam treated biomass may be mixed with other types and qualities of biomass, e.g. manure 1.11, before or during the process in the biogas reactor. The mixing may occur in a unit placed prior to the reactor, such as a power feed 1.4.

The biomass present in the biogas reactor will be degassed, and the nitrogen present in the produced gaseous phase may be further extracted and converted into applicable liquid N-fertilizer. For this, the gaseous phase comprising the volatile nitrogen containing compounds is subjected to N-stripping. In FIG. 6, the N-stripping process includes moving degassed biomass 1.12 using a screw press 1.5 and moving the gaseous phase to a N-stripper 1.7, and subsequently to a N-absorber 1.8, where the stripped gaseous nitrogen is absorbed and fixed in a liquid fertilizer 1.13.

The water part from the N-stripper and -absorber that is not fixed in the liquid fertilizer may be collected, and transferred to the reactor for producing biogas feedstock. The water may be transferred via the power feed 1.4 as indicated by arrow in FIG. 6, or via a "mixer and heater unit" as shown in FIG. 1.

The gaseous part from the N-absorber that is not fixed in the liquid fertilizer may be emitted to the surroundings, optionally using a bio-filter 1.14.

The gaseous parts are transferred between the units using ventilation means 1.6, 1.9. Examples of ventilation means include pumps and fans. The ventilation means may be operated by heated reject air 1.15.

Example 2: System Comprising N-Steamer

Figure 7:
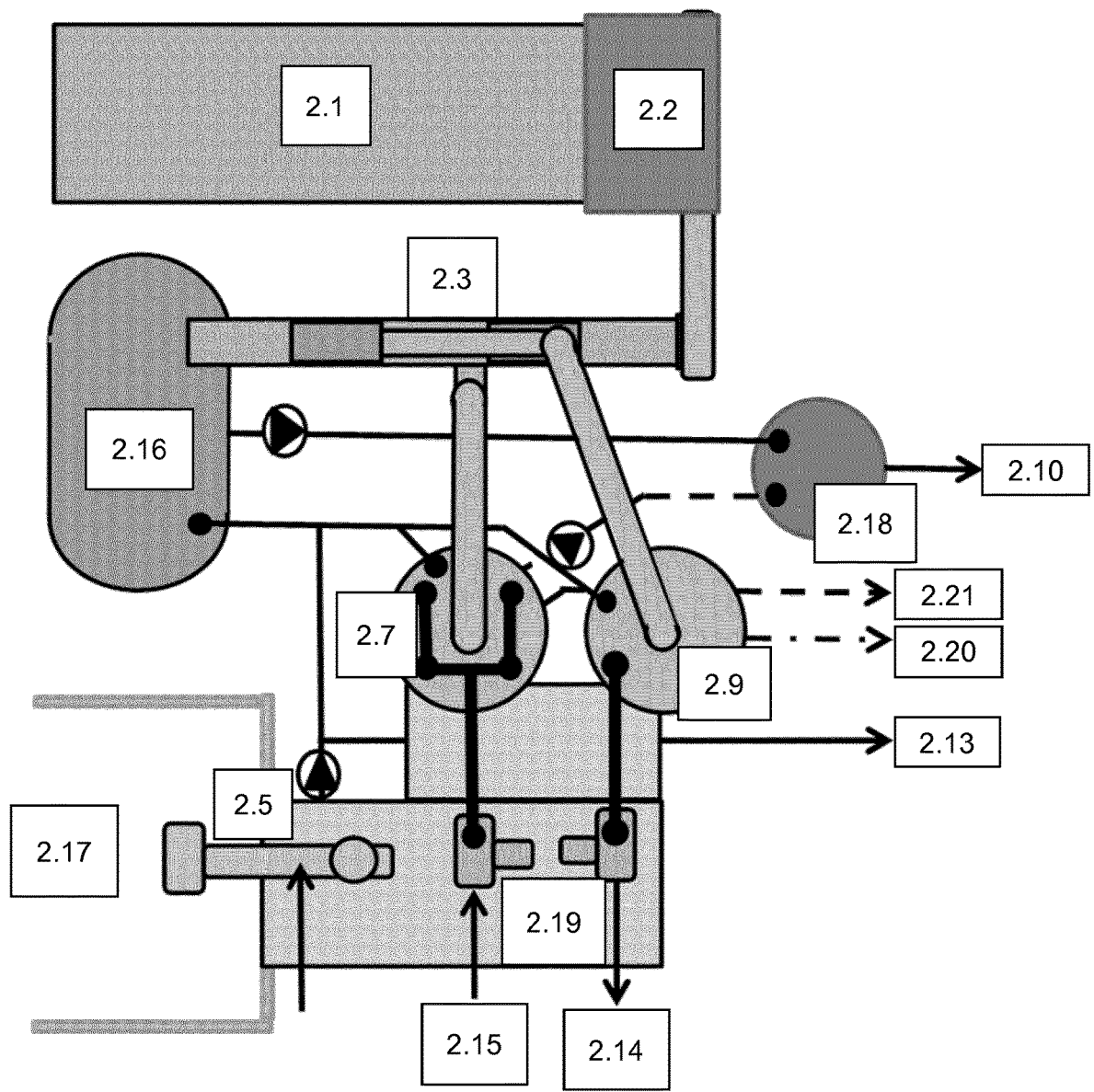
FIG. 7 shows an embodiment of a system for treating biomass comprising a continuously operating N-steamer 2.3, wherein the system further may be used to produce phosphorus (P) fertilizers. The Figure is further described in Example 2.

FIG. 7 shows another embodiment of a system for treating biomass comprising a continuously operating N-steamer 2.3, similar to the N-steamer of Example 1, and similar to Example 1 the steam comprising nitrogen used within the N-steamer may have any origin, and for example be a N-steam from a drying unit (not shown in FIG. 7).

The system of FIG. 7 is similar to Example 1 in that it also comprises a walking floor container 2.1, regulation means 2.2, screw press 2.5, N-stripping 2.7, N-absorber 2.9, biogas reactor 2.10, and ventilation means 2.19. The ventilation means may also be operated by heated reject air 2.15, and the stripped nitrogen may be fixed in a liquid fertlizer 2.13, and the residual gas emitted to the surrounding, optionally using a bio-filter 2.14.

In addition to the features similar to Example 1, the system of FIG. 2 further comprises a bio-mixer 2.16, a buffer storage for fibers 2.17, and a heater and mixer 2.18. The system of FIG. 7 may further result in further fertilizer products, such as nitrogen enriched liquid fertilizer 2.20, and phosphorus fertilizer 2.21.

The system and process shown in FIG. 7 may follow the following steps:

a) Degassed biomass is pumped to the screw press 2.5.
b) From the screw press, the solid fibers are pushed directly into the buffer storage 2.17, and from the buffer storage they may be transferred to the bio-mixer 2.16, a dryer unit or another place (not shown).
c) The reject liquid from the screw press is pumped to the N-stripper 2.7 and N-absorber 2.9, from where it may be stored before use as a fertilizer, and/or the reject liquid from the screw press is pumped to the bio-mixer 2.16.
d) Heated air is blown through the reject liquid placed within the N-stripper 2.7 with a pressure in the range of 600-2500 mmVs, such as a pressure of 600 mmVs using an access ventilation 2.19. The unit "mmVs" is also referred to as "millimetres of water column" or "[mmH$_2$O]".
e) N is stripped from the reject by heating to above 80° C. using heating means, optionally shaped as spirals, placed in the N-stripper, and by adjusting the pH to above 9 by adding a base, such as lime (CaCO$_3$).
f) The N steam is sucked from the N-stripper and through the N-steamer at a pressure in the range of −400 to −800 mmVs, such as a pressure of −400 mmVs.
g) Inorganic material and other components may be precipitated within the N-stripper, and pumped as sedimented phosphorus (P) for either concentration or dewatering, before use as fertilizer.
h) The N-stripped and heated reject from the N-stripper may be pumped to the heater and mixer 2.18, and thereby used to regulate the dry matter content and concentration of NH$_3$, NHa, and other components comprising nitrogen, within the heater and mixer.
i) The N-steamer is fed with biomass via the walking floor 2.1 and dosage system 2.2. The N-steamer may also be fed with degassed biomass, i.e. fibers from the buffer storage 2.17. While the biomass is moved continuously through the N-steamer, N-steam is sucked through the biomass to enable the ammonia pretreatment.
j) The N-steamed biomass is transferred to the bio-mixer 2.16, where it may be mixed with other types of biomass, such as manure from poultry, before being transferred to the heater and mixer 2.18, and then further to the biogas reactor 2.10.
k) The used N-steam exiting the N-steamer may be sucked to the N-absorber 2.9, wherein the nitrogen comprised in the steam may be bonded to the reject liquid, e.g. by addition of H$_2$SO$_4$.
l) The reject gas from the N-absorber may be emitted to the surroundings, e.g. by flowing it through a bio-filter at positive or negative pressure.

Example 3: N-Steamer Integrated with a Drying Unit

FIG. 8 shows an embodiment of a system for treating biomass comprising a continuously operating N-steamer 3.17. The embodiment of FIG. 8 shows how the N-steamer may be integrated and used for filtering and/or cleaning of steam/fluegas from a drying unit, in combination with production of biogas substrates.

Similar to Examples 1-2, the N-steamer 3.17 is fed with biomass, such as straw and/or manure e.g. from horses, from a walking floor container 3.15 and regulation means 3.16. The N-steamed biomass exiting from the N-steamer may be used as biogas substrate, and stored in a container for use 3.18.

FIG. 8 further shows that the N-steam used in the N-steamer is transferred from a drying unit 3.4, for example a drum dryer. The N-steam from the drying unit may be transferred to the N-steamer via a pump, e.g. a cyclon 3.5.

Similar to Examples 1-2 the system may further comprise N-stripper 3.7, N-absorber/scrubber 3.8, and ventilation means 3.6, 3.9 for extracting nitrogen from the reject gaseous phase, before the reject gaseous phase is emitted to the surroundings, e.g. through a bio-filter 3.14.

Thus, in the embodiment of FIG. 8, the N-steamer functions as a filtering- and fluegas cleaning unit for the reject steam from the drying unit. The reject steam a drying unit typically comprises heat, liquid, ammonia, and will have a bad smell. By using the reject steam for the N-steamer, the energy, liquid, ammonia and smell are bonded to the biomass within the N-steamer, and thus recycled back into the biomass product, instead of being emitted to the surroundings with the adverse environmental and worksafety consequences.

As shown in FIG. 8, the drying unit may be used for drying different types of biomass, e.g. degassed fibers and/or poultry manure 3.1, and/or agricultural biomass and/or bio fuel, such as chipped bark 3.2. The bio fuel may optionally be heat treated, for example in a burner 3.3, prior to being introduced into the drying unit.

Thus, the system of FIG. 8 may advantageously be integrated with production systems including poultry production.

The treated biomass from the drying unit, i.e. the dried fibers, may also be converted into additional products, such as substrate, litter, or fertilizer pellets 3.22. The dried fibers are first transferred from the drying unit 3.10, moved to a feed for a pellet press 3.11, and then pressed into pellets in the pellet press 3.12. The pellets are then optionally cooled and sorted 3.13, e.g. by sieving, and then they may be transferred to containers 3.14, such as big bags, and will be ready to use as substrate, litter or fertilizer pellets.

Thus, the system of FIG. 8 may advantageously be integrated with production systems including poultry production and/or litter and/or fertilizer pellet production.

Example 4: N-Steamer Integrated for Substrate and Mushroom Production

Figure 9:
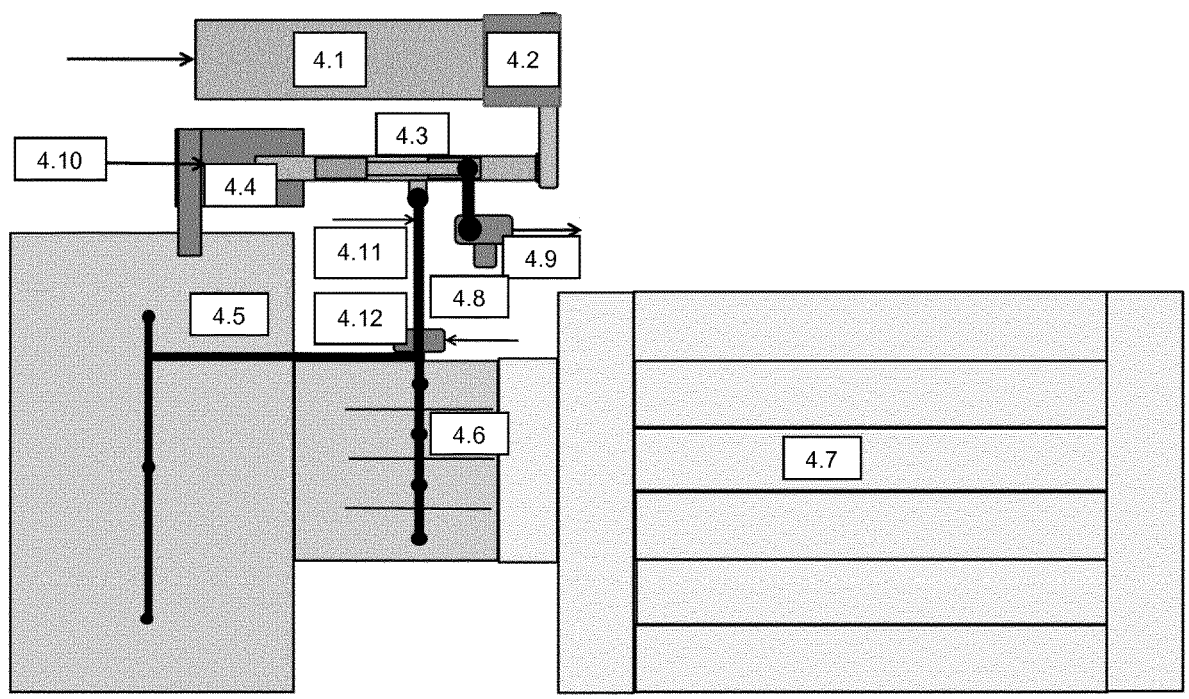
FIG. 9 shows an embodiment of a system for treating biomass comprising a continuously operating N-steamer 4.3. integrated with a system for substrate and mushroom production. The Figure is further described in Example 4.

FIG. 9 shows an embodiment of a system for treating biomass comprising a continuously operating N-steamer 4.3. integrated with a system for substrate and mushroom production.

Similar to Examples 1-3, the N-steamer may be fed with biomass, e.g. straw and manure from for examples horses, which is stored in a walking floor container 4.1, and transferred to the continuously operating N-steamer using regulation means 4.2. The N-steam treated biomass may be transferred to a mixing unit 4.4, and the used and rejected N-steam may be emitted to the surroundings, e.g. through a bio-filter, and/or exposed to N-stripping for extraction of nitrogen 3.9.

The N-steam treated biomass placed in the mixing unit may be further mixed with other biomass, e.g. fibers from degassed biomass 4.10.

The treated biomass may be transferred and stored in a composting unit 4.5, from where it may be transferred to a pasteurization unit, or pasteurization channels 4.6. Through the channels, the biomass may be provided with injection of ammonia water 4.11, and exhaustion of ammonia air 4.12, and/or a heating source and/or a heat exchanger 4.8. This way biomass with optimal properties for mushroom substrates may be produced. The system may therefore advantageously be combined with a mushroom production unit 4.7.

Example 5: N-Steamer for Biogas Substrate Production

Figure 10:
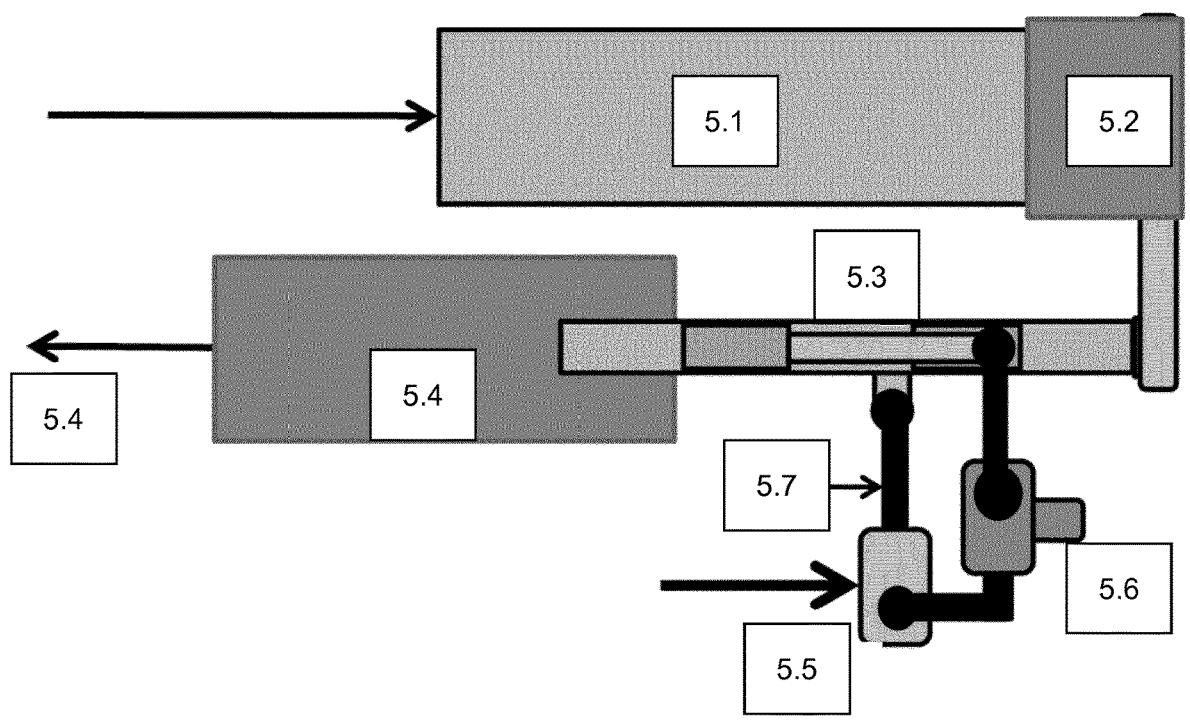
FIG. 10 shows an embodiment of a system for treating biomass comprising a continuously operating N-steamer 5.3. integrated with a system for biogas substrate production. The Figure is further described in Example 5.

FIG. 10 shows an embodiment of a system for treating biomass comprising a continuously operating N-steamer 5.3. integrated with a system for biogas substrate production.

Similar to Examples 1-4, the N-steamer may be fed with biomass, e.g. straw, which is stored in a walking floor container 5.1, and transferred to the continuously operating N-steamer using regulation means 5.2.

The N-steamer may be provided with N-steam, or ammonia water, which is injected into the N-steamer 5.7, and where the properties of the N-steam may be controlled using a source of heat and heat exchanger 5.5, and ventilation means 5.6.

The N-steam treated biomass from the N-steamer may be transferred to a container for biogas substrate 5.4, from where it may be further transferred as substrates for a biogas plant 5.8.

REFERENCES

[1] WO1609494
[2] WO 2016/116113

The invention claimed is:

1. A system for treating biomass, said system comprising:
    at least one conduit, the a least one conduit comprising:
        at least one biomass inlet and at least one biomass outlet, and
        at least one gas inlet and at least one gas outlet;
    a biomass transport unit configured to move the biomass in a longitudinal direction through the conduit(s) from the at least one biomass inlet to the at least one biomass outlet thereby defining a biomass transport direction wherein the transport unit comprises two or more transport planes configured to sandwich the biomass in-between said planes; and
    a gas flow configured to flow from the at least one gas inlet to the at least one gas outlet such that the gas flow from the gas inlet to the gas outlet is angled to the longitudinal direction of the conduit and the gas flow crosses the longitudinal biomass transport direction,
    wherein the transport unit comprises two or more conveyor belts, and the first of the conveyor belts defines a lower transport plane, and the second of the conveyor belts defines an upper transport plane, a distance between the first and second conveyor belts decreasing from the biomass inlet to the biomass outlet such that the transport unit is configured to accommodate an inherent change in compaction degree along the conduit or biomass transport direction, and
    wherein the at least one conduit is configured to tolerate a negative pressure of at least 0.1 bar, such that the gas flows from the at least one gas inlet to the at least one gas outlet at a negative pressure.

2. The system according to claim 1, wherein the at least one gas inlet is selected from the group of: air inlet, steam inlet, exhaust gas inlet, and wherein the at least one gas outlet is correspondingly selected from the group of: air outlet, steam outlet, exhaust gas outlet.

3. The system according to claim 1, further comprising a safety valve configured to be activated at a negative pressure of 0.1, 0.2, or 0.3 bar.

4. The system according to claim 1, wherein the biomass transport direction is along the longitudinal direction of the at least one conduit.

5. The system according to claim 1, wherein the at least one gas inlet and the at least one gas outlet are placed at opposite sides of the at least one conduit, such that the gas flows across the longitudinal direction of the at least one conduit.

6. The system according to claim 1, wherein the at least one gas inlet comprises two or more gas inlets, and the at least one gas outlet comprises two or more gas outlets.

7. The system according to claim 1, wherein the transport unit is configured to adapt to the compaction degree of the biomass.

8. The system according to claim 1, wherein the distance (s) between the two or more transport planes are controlled by an inclination ratio between the transport planes.

9. The system according to claim 1, wherein the transport unit is configured to a biomass retention time within the conduit of between 5 minutes to 12 hours, between 10 to 60 minutes, or-between 20 to 30 minutes.

10. The system according to claim 1, further comprising moisturising means at the biomass inlet for moisturising the biomass, and/or further comprising insulation, wherein the insulation encapsulate the at least one conduit fully or partly, and/or further comprising a dryer for drying a biomass, wherein the gas exhaust from the dryer is connected to the at least one steam inlet.

11. The system according to claim 1, wherein the transport unit is configured to be operated continuously, and/or wherein the transport unit comprises multiple openings for gas inlet and outlet, and a first conveyor belt defines a lower transport plane.

12. The system according to claim 11, wherein the first conveyor belt comprises multiple planar sections, wherein each planar section is angular displaced relative to the transport plane.

13. The system according to claim 12, wherein each planar section comprises a support element placed opposite the transport direction.

14. The system according to claim 13, wherein the support element is configured to secure the biomass.

15. The system according to claim 12, wherein the planar sections are fixated by at least one hinge, wherein the at least one hinge is placed at the edge of the planar section facing the transport direction.

16. The system according to claim 1, wherein the gas inlets and gas outlets are placed at the longitudinal sides of the conduit.

17. The system according to claim 1, wherein the conveyor belts are inclined from the biomass inlet to the biomass outlet such that the biomass outlet is above the biomass inlet.

* * * * *